United States Patent [19]
Patton et al.

[11] Patent Number: 5,997,848
[45] Date of Patent: *Dec. 7, 1999

[54] METHODS AND COMPOSITIONS FOR PULMONARY DELIVERY OF INSULIN

[75] Inventors: John S. Patton, San Carlos; Linda Foster, Sunnyvale; Robert M. Platz, Half Moon Bay, all of Calif.

[73] Assignee: Inhale Therapeutic Systems, San Carlos, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/821,493

[22] Filed: Mar. 21, 1997

Related U.S. Application Data

[63] Continuation of application No. 08/383,475, Feb. 1, 1995, abandoned, which is a continuation-in-part of application No. 08/207,472, Mar. 7, 1994, abandoned.

[51] Int. Cl.⁶ .............................. A61K 9/12; A61K 38/28
[52] U.S. Cl. .................................. 424/46; 424/43; 514/3; 514/866
[58] Field of Search .................... 424/44, 45, 46; 514/21, 2, 3, 866; 128/200.14, 200.18

[56] References Cited

U.S. PATENT DOCUMENTS

| | | |
|---|---|---|
| 2,598,525 | 5/1952 | Fox . |
| 3,202,731 | 8/1965 | Grevenstuk et al. . |
| 3,300,474 | 1/1967 | Flodin et al. . |
| 3,314,803 | 4/1967 | Tarrytown et al. . |
| 3,362,405 | 1/1968 | Hazel . |
| 3,425,600 | 2/1969 | Ablanalp . |
| 3,540,927 | 11/1970 | Niimi et al. . |
| 3,554,768 | 1/1971 | Feldman . |
| 3,620,776 | 11/1971 | Mishkin et al. . |
| 3,666,496 | 5/1972 | Honey et al. . |

(List continued on next page.)

FOREIGN PATENT DOCUMENTS

| | | |
|---|---|---|
| 902 257 | 8/1985 | Belgium . |
| 0 015 123 | 9/1980 | European Pat. Off. . |
| 0 072 046 | 2/1983 | European Pat. Off. . |
| 0 111 216 | 6/1984 | European Pat. Off. . |
| 0 140 489 | 5/1985 | European Pat. Off. . |
| 0 229 810 | 7/1987 | European Pat. Off. . |
| 0 237 507 | 9/1987 | European Pat. Off. . |
| 0 289 336 | 11/1988 | European Pat. Off. . |
| 0302772 | 2/1989 | European Pat. Off. ......... A61K 9/06 |
| 0 347 779 | 12/1989 | European Pat. Off. . |
| 0360 340 | 3/1990 | European Pat. Off. . |

(List continued on next page.)

OTHER PUBLICATIONS

Laube, B.L., et al. (1993) "Preliminary Study of the Efficacy of Insuling Aerosol Delivered by Oral Inhalation in Diabetic Patients" *JAMA* 269(16):2106–2109.

Liu, F., et al. (1993) "Pulmonary Delivery of Free and Lipo–somal Insulin" *Pharmaceutical Research* 10(2):228–232.

Hastings, R.H., et al. (1992) "Clearance of Different–Sized Proteins from the Alveolar Space in Humans and Rabbits" *J. Appl. Physiol.* 73:1310–1316.

Sakr, F. (1992) "A New Approach for Insulin Delivery via the Pulmonary Route: Design and Pharmcokinetics in Non–Diabetic Rabbits" *International Journal of Pharmaceuticals* 86:1–7.

Ryden, L., et al. (1992) "Effect of Polymers and Microspheres on the Nasal Absorption of Insulin in Rats" *International Journal of Pharmaceutics* 83:1–10.

(List continued on next page.)

*Primary Examiner*—Gollamudi S. Kishore
*Attorney, Agent, or Firm*—Townsend and Townsend and Crew LLP

[57] ABSTRACT

Systemic delivery of insulin to a mammalian host is accomplished by inhalation of a dry powder of insulin. It has been found that dry insulin powders are rapidly absorbed through the alveolar regions of the lungs.

7 Claims, 8 Drawing Sheets

U.S. PATENT DOCUMENTS

| | | |
|---|---|---|
| 3,764,716 | 10/1973 | Rainwater et al. . |
| 3,921,637 | 11/1975 | Bennie et al. . |
| 3,937,668 | 2/1976 | Zolle ........................................ 252/316 |
| 3,964,483 | 6/1976 | Mathes . |
| 3,971,852 | 7/1976 | Brenner et al. . |
| 3,991,304 | 11/1976 | Hillsman . |
| 3,991,761 | 11/1976 | Cocozza . |
| 3,994,421 | 11/1976 | Hansen . |
| 4,036,223 | 7/1977 | Obert . |
| 4,069,819 | 1/1978 | Valentini et al. . |
| 4,098,273 | 7/1978 | Glenn . |
| 4,109,019 | 8/1978 | Moore . |
| 4,153,689 | 5/1979 | Hiral et al. ............................. 424/178 |
| 4,206,200 | 6/1980 | Guthöhrlein et al. . |
| 4,249,526 | 2/1981 | Dean et al. . |
| 4,253,468 | 3/1981 | Lehmbeck . |
| 4,294,829 | 10/1981 | Suzuki et al. . |
| 4,338,931 | 7/1982 | Cavazza . |
| 4,423,079 | 12/1983 | Kline . |
| 4,446,862 | 5/1984 | Baum et al. . |
| 4,452,239 | 6/1984 | Malem . |
| 4,484,577 | 11/1984 | Sackner et al. . |
| 4,503,035 | 3/1985 | Pestka et al. . |
| 4,533,552 | 8/1985 | Kawamata et al. . |
| 4,534,343 | 8/1985 | Nowacki et al. . |
| 4,559,298 | 12/1985 | Fahy . |
| 4,590,206 | 5/1986 | Forrester et al. . |
| 4,599,311 | 7/1986 | Kawasaki . |
| 4,617,272 | 10/1986 | Kirkwood et al. . |
| 4,624,251 | 11/1986 | Miller . |
| 4,627,432 | 12/1986 | Newell et al. . |
| 4,649,911 | 3/1987 | Knight et al. . |
| 4,677,975 | 7/1987 | Edgar et al. . |
| 4,698,328 | 10/1987 | Neer et al. . |
| 4,719,762 | 1/1988 | Osabe . |
| 4,739,754 | 4/1988 | Shaner . |
| 4,790,305 | 12/1988 | Zoltan et al. . |
| 4,806,343 | 2/1989 | Carpenter et al. . |
| 4,807,814 | 2/1989 | Douche et al. . |
| 4,811,731 | 3/1989 | Newell et al. . |
| 4,819,629 | 4/1989 | Jonson . |
| 4,820,534 | 4/1989 | Saleeb et al. . |
| 4,823,784 | 4/1989 | Bordoni et al. . |
| 4,824,938 | 4/1989 | Koyama et al. . |
| 4,830,858 | 5/1989 | Payne et al. . |
| 4,833,125 | 5/1989 | Neer et al. . |
| 4,855,157 | 8/1989 | Tashiro et al. . |
| 4,857,319 | 8/1989 | Crowe et al. . |
| 4,876,241 | 10/1989 | Feldman et al. . |
| 4,884,565 | 12/1989 | Cocozza . |
| 4,889,114 | 12/1989 | Kladders . |
| 4,891,319 | 1/1990 | Roser . |
| 4,895,719 | 1/1990 | Radhakrishnan et al. ................ 424/45 |
| 4,897,353 | 1/1990 | Carpenter et al. . |
| 4,907,583 | 3/1990 | Wetterlin et al. . |
| 4,919,962 | 4/1990 | Arora et al. . |
| 4,926,852 | 5/1990 | Zoltan et al. . |
| 4,927,763 | 5/1990 | Sudoma et al. . |
| 4,931,361 | 6/1990 | Baldeschwieler et al. . |
| 4,942,544 | 7/1990 | McIntosh et al. . |
| 4,956,295 | 9/1990 | Sudoma . |
| 4,968,607 | 11/1990 | Dower et al. . |
| 4,984,158 | 1/1991 | Hillsman . |
| 4,995,385 | 2/1991 | Valentini et al. . |
| 5,011,678 | 4/1991 | Wang et al. ............................. 424/45 |
| 5,017,372 | 5/1991 | Hastings ................ 424/85.8 |
| 5,026,566 | 6/1991 | Foster . |
| 5,027,806 | 7/1991 | Zoltan et al. . |
| 5,033,463 | 7/1991 | Cocozza . |
| 5,035,237 | 7/1991 | Newell et al. . |
| 5,048,514 | 9/1991 | Ramella . |
| 5,049,388 | 9/1991 | Kright et al. . |
| 5,081,228 | 1/1992 | Dower et al. . |
| 5,093,316 | 3/1992 | Lezdey et al. . |
| 5,098,893 | 3/1992 | Franks et al. . |
| 5,099,833 | 3/1992 | Michaels . |
| 5,113,855 | 5/1992 | Newhouse . |
| 5,124,162 | 6/1992 | Bošković et al. . |
| 5,149,543 | 9/1992 | Cohen et al. . |
| 5,149,653 | 9/1992 | Roser . |
| 5,161,524 | 11/1992 | Evans . |
| 5,180,812 | 1/1993 | Dower et al. . |
| 5,186,164 | 2/1993 | Raghuprasad . |
| 5,200,399 | 4/1993 | Wettlaufer et al. . |
| 5,204,108 | 4/1993 | Illum ........................................ 424/434 |
| 5,206,200 | 4/1993 | Bush et al. . |
| 5,230,884 | 7/1993 | Evans et al. . |
| 5,253,468 | 10/1993 | Raymond . |
| 5,254,330 | 10/1993 | Ganderton ............................... 424/46 |
| 5,290,765 | 3/1994 | Wettlaufer et al. . |
| 5,295,479 | 3/1994 | Lankinen . |
| 5,302,581 | 4/1994 | Sarin et al. . |
| 5,309,900 | 5/1994 | Knoch et al. . |
| 5,320,094 | 6/1994 | Laube et al. . |
| 5,320,714 | 6/1994 | Brendel . |
| 5,331,953 | 7/1994 | Anderson et al. . |
| 5,354,562 | 10/1994 | Platz ........................................ 424/489 |
| 5,364,838 | 11/1994 | Rubsamen ................ 514/3 |
| 5,376,359 | 12/1994 | Johnson .................... 424/46 |
| 5,376,386 | 12/1994 | Ganderton ............................... 424/499 |
| 5,458,135 | 10/1995 | Patton ................ 128/200.14 |
| 5,506,203 | 4/1996 | Bäckström et al. . |
| 5,518,998 | 5/1996 | Bäckström et al. . |
| 5,672,581 | 9/1997 | Rubsamen et al. ...................... 514/3 |

FOREIGN PATENT DOCUMENTS

| | | |
|---|---|---|
| 0 366 303 | 5/1990 | European Pat. Off. . |
| 0 383 569 | 8/1990 | European Pat. Off. . |
| 0 467 172 | 1/1992 | European Pat. Off. . |
| 0 468 914 | 1/1992 | European Pat. Off. . |
| 0 490 797 | 6/1992 | European Pat. Off. . |
| 0 506 293 | 9/1992 | European Pat. Off. . |
| 0611567 | 8/1994 | European Pat. Off. ......... A61K 9/72 |
| 0655237 | 5/1995 | European Pat. Off. ......... A61K 9/00 |
| 2257351 | 1/1974 | France . |
| 18 12 574 | 6/1970 | Germany . |
| 24 15 159 | 10/1975 | Germany . |
| 31 41 498 | 4/1983 | Germany . |
| 01 61 072 | 9/1984 | Germany . |
| 59-095885 | 2/1984 | Japan . |
| 61-293201 | 12/1986 | Japan . |
| 7712041 | 5/1979 | Netherlands . |
| 883174 | 11/1981 | Russian Federation . |
| 94/0155 | 1/1994 | South Africa . |
| 84-03520 | 2/1983 | Spain . |
| 0628930 | 9/1978 | U.S.S.R. . |
| 1003926 | 3/1983 | U.S.S.R. . |
| 1 288 094 | 9/1972 | United Kingdom . |
| 1 477 775 | 6/1977 | United Kingdom . |
| 1527605 | 10/1978 | United Kingdom . |
| 2 105 189 | 3/1983 | United Kingdom . |
| 2 126 588 | 3/1984 | United Kingdom . |
| WO 84/00294 | 2/1984 | WIPO ................ A61K 9/14 |
| 86/04095 | 7/1986 | WIPO . |
| 87/00196 | 1/1987 | WIPO . |
| 87/05300 | 9/1987 | WIPO . |
| 8804556 | 6/1988 | WIPO . |
| WO 88/09163 | 12/1988 | WIPO . |
| 90/05182 | 5/1990 | WIPO . |
| 90/07351 | 7/1990 | WIPO . |
| 9009780 | 9/1990 | WIPO . |
| 90/15635 | 12/1990 | WIPO . |

| | | |
|---|---|---|
| 91/02558 | 3/1991 | WIPO . |
| 9102545 | 3/1991 | WIPO . |
| WO 91/06282 | 5/1991 | WIPO ............................. A61K 9/06 |
| 91/16038 | 10/1991 | WIPO . |
| 91/16882 | 11/1991 | WIPO . |
| WO 93/00951 | 1/1993 | WIPO ........................... A61M 11/00 |
| 9302712 | 2/1993 | WIPO . |
| 93/09832 | 5/1993 | WIPO . |
| 94/08552 | 4/1994 | WIPO . |
| WO 95/00127 | 1/1995 | WIPO ............................. A61K 9/72 |
| 95/23613 | 9/1995 | WIPO . |
| 96/09814 | 4/1996 | WIPO . |
| 97/03649 | 2/1997 | WIPO . |

OTHER PUBLICATIONS

Colthrope, P., et al. (1992) "The Pharmacokinetics of Pulmonary–Derived Insulin: A Comparison of Intratracheal and Aerosol Administration to the Rabbit" *Pharm. Res.* 9(6):764–768.

Pikal, M.J. (1992) "Polymorphism in Pharmaceutical Solids" AAPS, Annual Meeting and Exposition, Nov. 15–19, 1992.

Bjork, E., et al. (1988) "Degradable Starch Microspheres as a Nasal Delivery System for Insulin" *International Journal of Pharmaceutics* 47:233–238.

Elliott, R.B., et al. (1987) "Parental Absorption of Insulin for the Lung in Diabetic Children" *Aust. Paediatr. J.* 23: 293–297.

Chien, Y.W., et al. (1987) "Intranasal Drug Delivery for Systemic Medications" *CRC Critical Reviews in Therapeutic Drug Carrier Systems* 4(2):67–92.

Duchateau, G.S.M.J.E., et al. (1986) "Bile Salts and Intranasal Drug Absorption" *International Journal of Pharmaceutics* 31:193–199.

Nagano, M., et al. (1985) "New Methodo of Insulin Therapy: Transpulmonary Absorption of Insulin" *Jikeikal Med.* 32:503–506.

Nagai, T., et al. (1984) "Powder Dosage Form of Insulin for Nasal Administration" *Journal of Controlled Release* 1:15–22.

Schlute, K.J., et al. (1984) Abstract *Diabetes* 13(6):230–232.

Yoshida, H., et al. (1979) "Absorption of Insulin Delivered to Rabbit Trachea Using Aerosol Dosage Form" *Journal of Pharmaceutical Sciences* 68(5):670–671.

Lee, S.–W., et al. (1976) "Development of an Aerosol Dosage Form Containing Insulin" *Journal of Pharmaceutical Sciences* 65(4):567–572.

Wigley, F.M., et al. (1971) "Insulin Across Respiratory Mucosae by Aerosol Delivery" *Diabetes* 20(87):552–556.

Rao, A.R.G. (1959) "Aerosol Insulin Inhalation Enquiry" *Indian J. Physiol. Pharmacol.* 3:161–167.

Gansslen, M. (1925) "Uber Inhalation von Insulin" *Klin. Wochenschr.* 4:71 (with translation).

Andrews, Edmund L, "Gelatin Capsules Revamped For New Generation of Pills," *New York Times,* Saturday, Sep. 16, 1992, 19(n), 35(l), col 5, 9 col in.

Annear, D.I., "Observations on Drying Bacteria From the Frozen and From the Liquid State," *Austral. J. Exp. Biol.,* 1958, vol. 36, pp. 211–221.

Bohnet, Matthias, "Calculation and Design of Gas/Solid–Injectors," *Powder Tech.,* 1984, pp. 302–313.

Bone, S. and Pethig, R., "Dielectric Studies of Protein Hydration and Hydration–Induced Flexibility," *J. Mol. Biol.,* 1985, vol. 181, pp. 323–326.

Bruni, Fabio and A. Carl Leopold, "Glasss Transitions in Soybean Seed, Relevance to Anhydrous Biology," *Plant Physiol.,* 1991, vol. 96, pp. 660–663.

Budrik, G. K. et al., "Ejector Feeders for Pneumatic Transport Systems," *Chemical & Petroleum Engineering,* Sep.–Oct. 1978, vol. 14, Numbers 9–10, pp. 9–10.

Burke, Michael J., "The Glassy State and Survival of Anhydrous Biological Systems," *Membranes,* Metabolism and Dry Organisms, Appendix D, 1986, A. Carl Leopold Editor, pp. 358–363.

Byron, P. R. et al., "Drug Delivery Via the Respiratory Tract," *Journal of Aerosol Medicine,* 1994, vol. 7, No. 1, pp. 49–75.

Caffrey Martin et al., "Lipid–Sugar Interactions, Relevance to Anhydrous Biology," *Plant Physiol.,* 1988, vol. 86, pp. 754–758.

Carpenter, John F. et al., "Stabilization of Phosphofructokinase With Sugars During Freeze–Drying: Characterization of Enhanced Protection in the Presence of Divalent Cations," *Biochimica et Bipophysica Acta,* vol. 923, 1987, pp. 109–115.

Carpenter, John F. et al. "Stabilization of Phosphofructokinase During Air–Drying With Sugars and Sugar/Transition Metal Mixtures," *Cryobiology,* 1987, vol. 24, pp. 455–464.

Carpenter, John F. et al., "Modes of Stabilization of a Protein by Organic Solutes During Desiccation," *Cryobiology,* 1988, vol. 25, pp. 459–470.

Chopin, A. et al., "Destruction de *Microbacterium Lacticum, Escherichia coli* et *Staphylococcus Aureus* au cours du schage du lait par atomisation," *Can. Microbiol.,* 1977, 23:716–720. No translation.

Crowe, John H. et al., "Stabilization of Dry Phospholipid Bilayers and Proteins by Sugars," *Biochem. J.,* 1987, vol. 242, pp. 1–10.

Crowe, John H. et al., "Are Freezing and Dehydration Similar Stress Vectors? A comparison of Modes of Interaction of Stabilizing Solutes With Biomolecules," *Cryobiology,* 1990, vol. 27, pp. 219–231.

Fahy, Gregory M., "The Relevance of Cryoprotectant 'Toxicity' to Cryobiology," *Cryobiology,* 1986, vol. 23, pp. 1–13.

Finney, J. L. and P. L. Poole, "Protein Hydration and Enzyme Activity: The Role of Hydration Induced Conformation and Dynamic Changes in the Activity of Lysozyme," *Comments Mol. Cell. Biophys.,* 1984, vol. 2(3–4), pp. 129–151.

Flink, James M., Chapter 17 entitled "Structure and Structure Transitions in Dried Carbohydrate Materials," *Physical Properties of Foods,* 1983, M. Peleg and E. B. Bagley (Editions), pp. 473–521.

Fox, L. S. et al., "Performance of a Venturi Eductor as a Feeder in a Pneumatic Conveying System," *Powder & Bulk Engineering,* Mar. 1988, pp. 33–36.

Friedmann, T., "Progress Toward Human Gene Therapy," *Science* Jun. 16, 1989, vol. 244, pp. 1275–1281.

Gendler, Paul L. and Henry Rapoport, "Permethyk Analogue of the Pyrrolic Antibiotic Disctamycin A," *J. Med. Chem.,* 1981, vol. 24, No. 1, pp. 33–38.

Goetz, Philip W., Editor, Chapter Climate and Weather entitled "Atmospheric Humidity and Precipitation," *The New Encyclopedia Britannica,* vol. 16, Copyright 1985, pp. 476–479.

Green, J. L. and C. A. Angell, "Phase Relations and Vitrification in Saccharide–Water Solutions and The Trehalose Anomaly," *J. Phys. Chem.,* 1989, vol. 93, pp. 2880–2882.

Habener, Joel F., "Parthyroid Hormone: Secretion and Metabolism In Vivo," *Proc. Nat. Acad. Sci.,* USA, Dec. 1971, vol. 68, No. 12, pp. 2986–2991.

Heinemann, L., et al., "Time–Action Profile of Inhaled Insulin," *Diabetic Medicine,* 1997, vol. 14, pp. 63–72.

Herrington, B. L., "Some Physico–Chemical Properties of Lactose: The Spontaneous Crystallization of Super–Saturated Solutions of Lactose," *J. Dairy Science,* 1934, vol. 17, pp. 501–518.

Hesch, R. D., "Pulsatile Secretion of Parathyroid Hormone and Its Action on a Type I and Type II PTH Receptor: A Hypothesis for Understanding Osteoporosis," *Calcified Tissue Int.,* 1988, vol. 42, pp. 341–344.

Hubbard, Richard C. and Ronald G. Crystal, "Strategies for Aerosol Therapy of $\alpha^1$–Antitrypsin Deficiency by the Aerosol Route," *Lung,* 1990, vol. 168, Supplement 1990, Proceedings of the 8th Congress of SEP, Edited by H. Matthys, pp. 565–578.

Iijima, Teiji and Takesiii Sakane, "A Method for Preservation of Bacteria and Bacteriophages by Drying in Vacuo," *Cryobiology,* 1973, vol. 10, pp. 379–385.

Josic, Djuor, "Optimization of Process Conditions for the Production of Active Dry Yeast," *Lebensm–Wiss. U. Technol.,* 1982, vol. 15, No. 1, pp. 5–14.

Karel, M., "Water Relations of Foods," *R. B. Duckworth,* Ed., 1975, Academic Press, NY, pp. 648–649.

Kauzmann, Walter, "The Nature of the Glassy State and The Behavior of Liquids at Low Temperatures," Department of Chemistry, Princeton University, Princetown, New Jersey, Received Mar. 1, 1948, pp. 219–227.

Kim, Suk Shin and Santi R. Bhowmik, "Survival of Lactic Acid Bacteria During Spray Drying of Plain Yogurt," *Journal of Food Science,* vol. 55, No. 4, 1990, pp. 1008–10, 1048.

Kóhler, DIeter, Chapter 12 entitled "Systemic Therapy With Aerosols," *Aerosols in Medicine, Principles, Diagnosis and Therapy,* 2d ed., 1993, published by Elsevier, pp. 303–319.

Levine, Harry et al., "Principles of 'Cryostabilization' Technology From Structure/Property Relationships of Carbohydrate/Water Systems," *Cryo–letters,* 1988, vol. 9, pp. 21–63.

Malik, K. A. "A Simplified Liquid–Drying Method for the Preservation of Microorganisms Sensitive to Freezing and Freeze–Drying," *Journal of Microbiological Methods,* 1990, vol. 12, pp. 125–132.

Metwally, M. M. et al., "Spray Drying of Lactic Acid Culture, I. The Effect of Spray Drying Conditions on the Survival of Microorganisms," *Egyptian J. Dairy Sci.,* 1989, vol. 17, pp. 35–43.

Metwally, M. M. et al., "Spray Drying of Lactic Acid Cultures, II. The Effect of Culture Conditions and Storage on Microorganisms," *Ehyptian J. Diary Sci.,* 1989, vol. 17, pp. 273–275, 278.

Mumenthaler, Marco et al., "Feasibility Study on Spray–Drying Protein Pharmaceuticals: Recombinant Human Growth Hormone and Tissue–Type Plasminogen Activator," *Pharmaceutical Research,* 1994, vol. 11, No. 1, Plenum Publishing Corporation, pp. 12–20.

Neer, R. M. et al., "The Use of Parathyroid Hormone Plus 1,25–Dihydroxyvitamin D to Increase Trabecular Bone in Osteoporotic Men and Postmenopausal Women," *Osteoporosis,* 1987, vol. 53, pp. 829–835.

Nieminen, M. M. et al., "Aerosol Deposition in Automatic Dosimeter Nebulization," *Eur. J. Respir. DIs.,* 1987, vol. 71, pp. 145–152.

Patton, John S. et al., "(D) Routes of Delivery: Case Studies—(2) Pulmonary Delivery of Peptides and Proteins for Systemic Action," *Advanced Drug Delivery Reviews,* 1992, vol. 8, pp. 179–196.

Peri, C. et al., "Thermodynamics of Water Sorption on *Sacc. Cerevisiae* and Cell Viability During Spray–Drying," *Lebensm—Wiss. U. Technol.,* 1974, vol. 7, No. 2, pp. 76–81.

Pharmacia LKB Biotechnology Brochure entitled "A Cure For The Common Cold—Ready To Go DNA Labelling Kit Pre–Mixed Reactions That Store At Room Temperature," Undated, 9 pages.

Pikal, Michael J., "Polymorphisms in Pharmaceutical Solids," *AAPS,* Nov. 15–19, 1992, Annual Meeting and Expositions, San Antonio, TX, 2 pages.

Pittman, A. N. et al., "Pneumatic Conveying of Bulk Solids Using a Vacuum Aerated Feed Nozzle," *Solid Handling Conference Paper C4,* Jun. 10–12, 1986, Thames Polytechnic London, United Kingdom, pp. C41–C51.

Poole, P. L. et al., "Sequential Hydration of a Dry Globular Protein," *Biopolymers,* 1983, vol. 22, pp. 255–260.

Poole, P. L. et al., "Hydration–Induced Conformational and Flexibility Changes in Lysozyme at Low Water Contents," *Int. J. Biol. Macromol.,* Oct. 1983, vol. 5, pp. 308–310.

Prajapati, J. B. et al., "Survival of Lactobacillus Acidophilus in Blended—Spray Dried Acidophilus Preparations," *Australian Journal of Dairy Technology,* Mar./Jun. 1987, pp. 17–21.

Roos, Y et al., "Effects of Glass Transitions on Dynamic Phenomena, Figure 10.8," *The Glassy State in Foods,* published by J. M. Blanchard and P. J. Lillford (Nillington University Press), 1993, one page.

Rosenfeld, Melissa A. et al., "Adenovirus–Mediated Transfer of a Recombinant $\alpha$–1–Antitrypsin Gene To The Lung Epithelium in Vivo," *Science,* vol. 252, 19 Apr. 1991, pp. 431–434.

Roser, Bruce, "Trehalose Drying: A Novel Replacement For Freeze–Drying," *Biopharm.,* Sep. 1991, vol. 4, No. 8, pp. 47–53.

Schneider, Z. et al., "Thermostability of Enzyme in the Three–Dimensional Network of Polisaccharide Chains," *Bulletin de l'Academie Polonaise des Sciences,* 1968, C1. II, vol. XVI, No. 4, 1968, Serie des Sciences Biologiques, pp. 203–204.

Skrabanja, Arno et al., "Lyophilization of Biotechnology Products," *PDA Journal of Pharmaceutical Science & Technology,* Nov.–Dec. 1994, vol. 48, No. 6, pp. 311–317.

Slade, Louise et al., "Structural Stability of Intermediate Moisture Foods—A New Understanding?" *Food Structure, Its Creation and Evaluation,* 1988, pp. 115–147.

Stribling et al., "The Mouse As a Model For Cationic Liposome–Based, Aerosolized Gene Delivery," *Journal of Biopharmaceutical Sciences,* 1992, 3(1/2), pp. 255–263.

Tertyshny, V. N. et al., "Effect of Orthophosphoric Acid on Survivability of Proionibacterium Shermanii After Spray Drying And In The Process of Storage," *Microbiology Journal,* 1988, vol. 50, No. 3, pp. 49–52, English Summary on p. 52.

Townsend, Michael et al., "Use of Lyoprotectants in The Freeze–Drying of a Model Protein, Ribonuclease A," *Journal of Parenteral Sciences & Technology,* Nov.–Dec. 1988, vol. 42, No. 6, pp. 190–199.

Tsourouflis, Spyros et al., "Loss of Structure in Freeze–Dried Carbohydrates Solutions: Effect of Temperature, Moisture Content and Composition," *J. Sci. Fd Agric.,* 1976, vol. 27, pp. 509–519.

Uedaira, Hatsuho et al., "The Effect of Sugars On The Thermal Denaturation of Lysozyme," *Bulletin of The Chemical Society of Japan,* Sep. 1980, vol. 53, pp. 2451–2455.

Underwood, Stephen et al., "A Novel Technique For The Administration of Bronchodilator Drugs Formulated As Dry Powders to the Anaesthetized Guinea Pig," *Journal of Pharmacological Methods,* 1991, vol. 26, pp. 203–210.

Van de Beek, M. J. et al., "Preservation of the Enzymatic Activity of Rennin During Spray Drying and During Storages, And The Effect of Sugars And Certain Other Activities," *Neth. Milk Dairy J.,* 1969, vol. 23, pp. 46–54.

Wettlaufer, Scott H. et al., "Relevance of Amadori And Maillard Products To Seed Deterioration," *Plant Physiol.,* Apr. 1991, vol. 97, pp. 165–169.

White, G. W. et al., "The Glassy State in Certain Sugar–Containing Food Products," *J. Food Technol.,* vol. 1, pp. 73–92.

Williams, Adeyinka et al., "Vial Breakage by Frozen Mannitol Solutions: Correlation With Terminal Characteristics And Effect of Stereoisomerism, Additives, and Vial Configuration," *Journal of Parenteral Science & Technology,* Mar.–Apr. 1991, vol. 45, No. 2, pp. 94–100.

Williams, Robert J. et al., "The Glassy State in Corn Embryos," *Plant Physiol.,* 1989, vol. 89, pp. 977–981.

Witham, Clyde L., "Dry Dispersion With Sonic Velocity Nozzles," *Workshop on Dissemination Techniques for Smoke and Obscurants Chemical Systems Laboratory,* Aberdeen Proving Group, MD, Mar. 14–16, 1983, pp. 1–26.

Zholob, V. M. et al., "Effect of Injector Unit Design On The Particle Size of Atomized Powder," 0038–5735/79/1806, 1979 Plenum Publishing Corporation, pp. 362–364, Dnepropetrovsk State University, Translated from *Poroshkovaya Metallurgiya,* Jun. 1979, No. 6(198), pp. 13–16, original article submitted Aug. 1, 1978.

Abstract—Japanese Patents Gazette—Week 8604—Apr. 12, 1985, Section Chemical JP 60244288–A, Applicant: Okura Seiyaku KK, one pages, and translation in English.

Abstract—Japanese Patents Gazette—Week 8746—Jul 10, 1987, Section Chemical JP 62228272–A, Applicant: Amano Pharm. KK, one page.

Abstract—Japanese Patents Gazette—Week 8750—Section Chemical JP 62255434–A Fuji Seiyu KK—Nov. 7, 1987—Inventors: Tagawa Kunio and Kurosawa Wahei—Applicant: Fuji Oil Co Ltd.

Abstracts, 18th Anuual Meeting, *Cryobiology,* vol. 18, No. 6, Dec. 1981, see Numbers 20 page 617 & 24 page 618, Author Gregory Fahy.

"Clean–Up With Pulsed Jets," *Manufacturing Chemist,* Apr. 1992, pp. 29, 31.

"Production of Trehalose Dried Eggs," D5, Tg Measurements, Undated, 10 pages.

Drytec, Compact Laboratory Dryer, Undated Brochure, one page.

Lab–Plant Ltd., SD–04 Laboratory Scale Spray Drier, Undated Brochure, 4 pages.

Kohler Diabetes JADA, Feb. 1984 (Abst.).

METHODS AND COMPOSITIONS FOR PULMONARY DELIVERY OF INSULIN

This is a Continuation of application Ser. No. 08/383,475 filed Feb. 1, 1995, now abandoned, which is a continuation-in-part of application Ser. No. 08/207,472, filed Mar. 7, 1994 now abandoned, the disclosures of which are incorporated by reference.

BACKGROUND OF THE INVENTION

1. Field of the Invention

The present invention relates generally to methods and compositions for the respiratory delivery of insulin to diabetic patients. More particularly, the present invention relates to the pulmonary delivery of dry powder insulin preparations for rapid systemic absorption through the lungs.

Insulin is a 50 amino acid polypeptide hormone having a molecular weight of about 6,000 which is produced in the pancreatic β-cells of normal (non-diabetic) individuals. Insulin is necessary for regulating carbohydrate metabolism by reducing blood glucose levels, and a systemic deficiency causes diabetes. Survival of diabetic patients depends on the frequent and long-term administration of insulin to maintain acceptable blood glucose levels.

Insulin is most commonly administered by subcutaneous injection, typically into the abdomen or upper thighs. In order to maintain acceptable blood glucose levels, it is often necessary to inject insulin at least once or twice per day, with supplemental injections of rapid-acting insulin being administered when necessary. Aggressive treatment of diabetes can require even more frequent injections, where the patient closely monitors blood glucose levels using home diagnostic kits. The present invention is particularly concerned with the administration of rapid acting insulins which are able to provide serum insulin peaks within one hour and glucose troughs within 90 minutes.

The administration of insulin by injection is undesirable in a number of respects. First, many patients find it difficult and burdensome to inject themselves as frequently as necessary to maintain acceptable blood glucose levels. Such reluctance can lead to non-compliance, which in the most serious cases can be life-threatening. Moreover, systemic absorption of insulin from subcutaneous injection is relatively slow, frequently requiring from 45 to 90 minutes, even when fast-acting insulin formulations are employed. Thus, it has long been a goal to provide alternative insulin formulations and routes of administration which avoid the need for self-injection and which can provide rapid systemic availability of the insulin.

A variety of such alternative insulin administration roots have been proposed, including intranasal, intrarectal, and intravaginal.

While these techniques avoid the discomfort and poor compliance associated with subcutaneous injection, they each suffer from their own limitations. Intrarectal and intravaginal are inconvenient, uncomfortable, and the latter is not available to the entire population of diabetics. Intranasal delivery would be convenient and probably less objectionable than injection, but requires the use of potentially toxic "penetration enhancers" to effect passage of insulin across the nasal mucosa, which is characterized by a thick epithelial layer which is resistant to the passage of macromolecules. Of particular interest to the present invention is pulmonary insulin delivery where a patient inhales an insulin formulation and systemic absorption occurs through the thin layer of epithelial cells in the alveolar regions of the lung. Such pulmonary insulin delivery appears to provide more rapid systemic availability than does subcutaneous injection and avoids the use of a needle. Pulmonary insulin delivery, however, has yet to achieve widespread acceptance. Heretofore, pulmonary delivery has been most often accomplished through nebulization of liquid insulin formulations, requiring the use of cumbersome liquid nebulizers. Moreover, the aerosols formed by such nebulizers have a very low insulin concentration, necessitating a large number of inhalations to provide an adequate dosage. Insulin concentration is limited due to the low solubility of insulin in suitable aqueous solutions. In some cases, as many as 80 or more breaths may be required to achieve an adequate dosage, resulting in an administration time from 10 to 20 minutes, or more.

It would be desirable to provide improved methods and compositions for the pulmonary delivery of insulin. It would be particularly desirable if such methods and compositions were sufficiently convenient to permit self-administration even away from home and were able to deliver a desired total dosage with a relatively low number of breaths, preferably fewer than ten. Such methods and compositions should also provide for rapid systemic absorption of the insulin, preferably reaching a serum peak within 45 minutes or less and a resulting glucose trough within about one hour or less. Such rapid acting formulations will preferably be suitable for use in aggressive treatment protocols where injection of intermediate and long-acting insulin can be reduced or eliminated. The compositions of the present invention should also be stable, preferably consisting of a concentrated dry powder formulation.

2. Description of the Background Art

The respiratory delivery of aerosolized aqueous insulin solutions is described in a number of references, beginning with Gänsslen (1925) *Klin. Wochenschr.* 4:71 and including Laube et al. (1993) *JAMA* 269:2106–21–9; Elliott et al. (1987) *Aust. Paediatr. J.* 23:293–297; Wigley et al. (1971) *Diabetes* 20:552–556. Corthorpe et al. (1992) *Pharm Res* 9:764–768; Govinda (1959) *Indian J. Physiol. Pharmacol.* 3:161–167; Hastings et al. (1992) *J. Appl. Physiol.* 73:1310–1316; Liu et al. (1993) *JAMA* 269:2106–2109; Nagano et al. (1985) Jikeikai *Med. J.* 32:503–506; Sakr (1992) *Int. J. Phar.* 86:1–7; and Yoshida et al. (1987) *Clin. Res.* 35:160–166. Pulmonary delivery of dry powder medicaments, such as insulin, in a large particle carrier vehicle is described in U.S. Pat. No. 5,254,330. A metered dose inhaler (MDI) for delivering crystalline insulin suspended in a propellant is described in Lee and Sciara (1976) *J. Pharm. Sci.* 65:567–572. A MDI for delivering insulin into a spacer for regulating inhalation flow rate is described in U.S. Pat. No. 5,320,094. The intrabronchial administration of recombinant insulin is briefly described in Schluter et al. (Abstract) (1984) *Diabetes* 33:75A and Kühler et al. (1987) *Atemw. Lungenkrkh.* 13:230–232. Intranasal and respiratory delivery of a variety of polypeptides, including insulin, in the presence of an enhancer, are described in U.S. Pat. No. 5,011,678 and Nagai et al. (1984) *J. Contr. Rel.* 1:15–22. Intranasal delivery of insulin in the presence of enhancers and/or contained in controlled release formulations are described in U.S. Pat. Nos. 5,204,108; 4,294,829; and 4,153,689; PCT Applications WO 93/02712, WO 91/02545, WO 90/09780, and WO 88/04556; British Patent 1,527,605; Rydén and Edman (1992) *Int. J. Pharm.* 83:1–10; and Björk and Edman (1988) *Int. J. Pharm.* 47:233–238. The preparation and stability of amorphous insulin were described by Rigsbee and Pikal at the American Association of Pharmaceutical Sciences (AAPS), Nov. 14–18, 1993, Lake Buena Vista, Fla. Methods for spray drying polypeptide, polynucleotide and other labile drugs in a carrier which forms an amorphous structure which stabilize the drug are described in European patent application 520 748.

SUMMARY OF THE INVENTION

According to the present invention, methods and compositions for the aerosolization and systemic delivery of insulin to a mammalian host, particularly a human patient suffering from diabetes, provide for rapid absorption into blood circulation while avoiding subcutaneous injection. In particular, the methods of the present invention rely on pulmonary delivery of insulin in the form of a dry powder. Surprisingly, it has been found that inhaled dry insulin powders are deposited in the alveolar regions of the lung and rapidly absorbed through the epithelial cells of the alveolar region into blood circulation. Thus, pulmonary delivery of insulin powders can be an effective alternative to administration by subcutaneous injection.

In a first aspect of the present invention, insulin is provided as a dry powder, usually but not necessarily in a substantially amorphous state, and dispersed in an air or other physiologically acceptable gas stream to form an aerosol. The aerosol is captured in a chamber having a mouthpiece, where it is available for a subsequent inhalation by a patient. Optionally, the dry powder insulin is combined with a pharmaceutically acceptable dry powder carrier, as described in more detail below. The insulin powder preferably comprises particles having a diameter less then 10 $\mu$m, more preferably less than 7.5 $\mu$m, and most preferably below 5 $\mu$m, usually being in the range from 0.1 $\mu$m to 5 $\mu$m. Surprisingly, it has been found that the dry powder insulin compositions of the present invention are absorbed in the lung without the use of penetration enhancers such as those required for absorption through the nasal mucosa and upper respiratory tract.

In a second aspect, the present invention provides insulin compositions consisting essentially of dry powder insulin having an average particle size below 10 $\mu$m which may be combined with dry powder pharmaceutical carriers. The insulin composition is preferably free from penetration enhancers and comprises particles having a diameter less than 10 $\mu$m, preferably less than 7.5 $\mu$m, and most preferably below 5 $\mu$m, usually being in the range from 0.1 $\mu$m to 5 $\mu$m. Usually, the insulin dry powder will have from 5% to 99% by weight insulin in the composition, more usually from 15% to 80%, in a suitable pharmaceutical carrier, usually a carbohydrate, an organic salt, an amino acid, peptide, or protein, as described in more detail hereinafter.

In a third aspect of the present invention, insulin dry powders are prepared by dissolving insulin in an aqueous buffer to form a solution and spray drying the solution to produce substantially amorphous particles having a particle size less than 10 $\mu$m, preferably less than 7.5 $\mu$m, and most preferably below 5 $\mu$m, usually being in the range from 0.1 $\mu$m to 5 $\mu$m. Optionally, the pharmaceutical carrier is also dissolved in the buffer, to form a homogeneous solution, wherein spray drying of the solution produces individual particles comprising insulin, carrier buffer, and any other components which were present in the solution. Preferably the carrier is a carbohydrate, organic salt, amino acid, peptide, or protein which produces a substantially amorphous structure upon spray drying. The amorphous carrier may be either glassy or rubbery and enhances stability of the insulin during storage. Advantageously, such stabilized formulations are also able to effectively deliver insulin to the blood stream upon inhalation to the alveolar regions of the lungs.

A further understanding of the nature and advantages of the invention will become apparent by reference to the remaining portions of the specification and drawings.

BRIEF DESCRIPTION OF THE DRAWINGS

FIG. 8A is a chromatograph of an insulin standard stressed in 10 mM HCl at 25° C., showing human insulin eluting at 23.87 minutes desamido insulin eluting at 30.47 minutes. FIG. 8B shows a similar chromatogram of a human insulin standard. FIG. 8C shows a similar chromatogram of reconstituted, spray-dried insulin formulation prepared according to the present invention.

DETAILED DESCRIPTION OF SPECIFIC EMBODIMENTS

Figure 1:
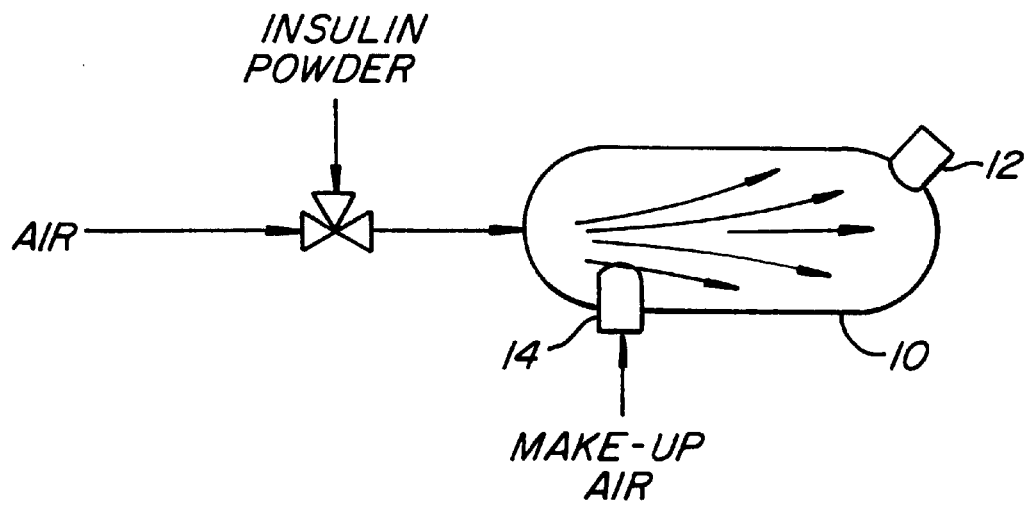
FIG. 1 is a schematic illustration of a system for aerosolizing a dose of insulin according to the method of the present invention.

According to the present invention, insulin is provided as a dry power. By "dry powder" it is meant that the moisture content of the powder is below about 10% by weight, usually below about 5% by weight, and preferably being below about 3% by weight. By "powder," it is meant that the insulin comprises free flowing particulates having a size selected to permit penetration into the alveoli of the lungs, preferably being less than 10 μm in diameter, preferably less than 7.5 μm, and most preferably less than 5μm, and usually being in the range from 0.1 μm to 5 μm in diameter.

The present invention is based at least in part on the unexpected observation that dry powder insulins are readily and rapidly absorbed through the lungs of a host. It was surprising that dry powder insulins could reach the alveolar region of the lungs, as water-soluble drugs such as insulin particles are known to be hygroscopic. See, e.g. Byron, ed., *Respiratory Drug Delivery,* CRC Press, Boca Raton (1990), p. 150. Thus, it would have been expected that as the particles passed through the airways of the lung (which has a relative humidity in excess of 99% at 37° C.), the individual particles would have a tendency to absorb water and grow to an effective particle size larger than the 10 μm upper limit of the present invention. If a substantial fraction of the insulin particles were larger than the target size range, it would be expected that the particles would deposit within the central airways of the lungs rather than the alveolar region, thus limiting delivery and subsequent systemic absorption. Moreover, the fluid layer over the epithelial cells of the lungs is very thin, usually a fraction of the diameter of the insulin powders being delivered. Thus, it was unpredictable prior to the present invention whether the dry insulin particles would dissolve upon deposition within the alveolar regions of the lungs. Surprisingly, the dry insulin powders are apparently able to both penetrate into the alveolar regions of the lungs and dissolve once they have deposited within the alveolar region of the lung. The dissolved insulin is then able to cross the epithelial cells into circulation.

It is presently believed that the effective absorption of insulin results from a rapid dissolution in the ultrathin (<0.1 μm) fluid layer of the alveolar lining. The particles of the present invention thus have a mean size which is from 10 to 50 times larger than the lung fluid layer, making it unexpected that the particles are dissolved and the insulin systemically absorbed in a rapid manner. Indeed, as shown in the Experimental section hereinafter, the dry insulin formulations of the present invention can provide even more rapid serum insulin peaks and glucose troughs than afforded by subcutaneous injection, which is presently the most common form of administration. An understanding of the precise mechanism, however, is not necessary for practicing the present invention as described herein.

Preferred compositions according to the present invention will be substantially free from penetration enhancers. "Penetration enhancers" are surface active compounds which promote penetration of insulin (or other drugs) through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurohydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. Surprisingly, it has been found that the dry powder insulin compositions of the present invention are readily absorbed in the lungs without the need to employ penetration enhancers.

Insulin dry powders suitable for use in the present invention include amorphous insulins, crystalline insulins, and mixtures of both amorphous and crystalline insulins. Dry powder insulins are preferably prepared by spray drying under conditions which result in a substantially amorphous powder having a particle size within the above-stated range. Alternatively, amorphous insulins could be prepared by lyophilization (freeze-drying), vacuum drying, or evaporative drying of a suitable insulin solution under conditions to produce the amorphous structure. The amorphous insulin so produced can then be ground or milled to produce particles within the desired size range. Crystalline dry powder insulins may be formed by grinding or jet milling of bulk crystalline insulin. The preferred method for forming insulin powders comprising particulates in the desired size range is spray drying, where pure, bulk insulin (usually in a crystalline form) is first dissolved in a physiologically acceptable aqueous buffer, typically a citrate buffer having a pH in the range from about 2 to 9. The insulin is dissolved at a concentration from 0.01% by weight to 1% by weight, usually from 0.1% to 0.2%. The solutions may then be spray dried in conventional spray drying equipment from commercial suppliers, such as Buchi, Niro, and the like, resulting in a substantially amorphous particulate product.

The dry insulin powders may consist essentially of insulin particles within the requisite size range and be substantially free from any other biologically active components, pharmaceutical carriers, and the like. Such "neat" formulations may include minor components, such as preservatives, present in low amounts, typically below 10% by weight and usually below 5% by weight. Using such neat formulations, the number of inhalations required for even high dosages can be substantially reduced, often to only a single breath.

The insulin powders of the present invention may optionally be combined with pharmaceutical carriers or excipients which are suitable for respiratory and pulmonary administration. Such carriers may serve simply as bulking agents when it is desired to reduce the insulin concentration in the powder which is being delivered to a patient, but may also serve to enhance the stability of the insulin compositions and to improve the dispersability of the powder within a powder dispersion device in order to provide more efficient and reproducible delivery of the insulin and to improve handling characteristics of the insulin such as flowability and consistency to facilitate manufacturing and powder filling.

Suitable carrier materials may be in the form of an amorphous powder, a crystalline powder, or a combination of amorphous and crystalline powders. Suitable materials include carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins, such as aspartame, human serum albumin, gelatin, and the like; (e) alditols, such as mannitol, xylitol, and the like. A preferred group of carriers includes lactose, trehalose, raffinose, maltodextrins, glycine, sodium citrate, tromethamine hydrochloride, human serum albumin, and mannitol.

Such carrier materials may be combined with the insulin prior to spray drying, i.e., by adding the carrier material to the buffer solution which is prepared for spray drying. In that way, the carrier material will be formed simultaneously with and as part of the insulin particles. Typically, when the carrier is formed by spray drying together with the insulin, the insulin will be present in each individual particle at a weight percent in the range from 5% to 95%, preferably from 20% to 80%. The remainder of the particle will primarily be carrier material (typically being from 5% to 95%, usually being from 20% to 80% by weight), but will also include buffer(s) and may include other components as described above. The presence of carrier material in the particles which are delivered to the alveolar region of the lung (i.e., those in the requisite size range below 10 μm) has been found not to significantly interfere with systemic absorption of insulin.

Alternatively, the carriers may be separately prepared in a dry powder form and combined with the dry powder insulin by blending. The separately prepared powder carriers will usually be crystalline (to avoid water absorption), but might in some cases be amorphous or mixtures of crystalline and amorphous. The size of the carrier particles may be selected to improve the flowability of the insulin powder, typically being in the range from 25 μm to 100 μm. Carrier particles in this size range will generally not penetrate into the alveolar region of the lung and will often separate from the insulin in the delivery device prior to inhalation. Thus, the particles which penetrate into the alveolar region of the lung will consist essentially of insulin and buffer. A preferred carrier material is crystalline mannitol having a size in the above-stated range.

The dry insulin powders of the present inventions may also be combined with other active components. For example, it may be desirable to combine small amounts of amylin or active amylin analogues in the insulin powders to improve the treatment of diabetes. Amylin-is a hormone which is secreted with insulin from the pancreatic β-cells in normal (non-diabetic) individuals. It is believed that amylin modulates insulin activity in vivo, and it has been proposed that simultaneous administration of amylin with insulin could improve blood glucose control. Combining dry powder amylin with insulin in the compositions of the present invention will provide a particularly convenient product for achieving such simultaneous administration. Amylin may be combined with insulin at from 0.1% by weight to 10% by weight (based on the total weight of insulin in a dose), preferably from 0.5% by weight to 2.5% by weight. Amylin is available from commercial suppliers, such as Amylin Corporation, San Diego, Calif., and can be readily formulated in the compositions of the present invention. For example, amylin may be dissolved in aqueous or other suitable solutions together with the insulin, and optionally carriers, and the solution spray dried to produce the powder product.

Figure 2:
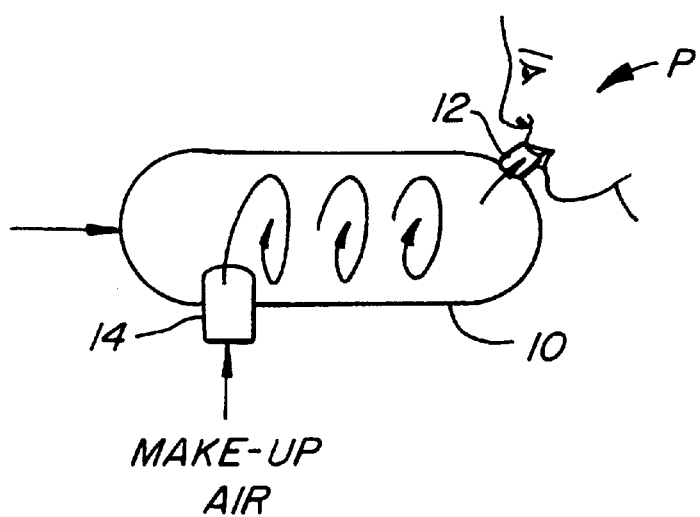
FIG. 2 is a schematic illustration of a patient inhaling an aerosolized dose of insulin from the system of FIG. 1.

The dry powder insulin compositions of the present invention are preferably aerosolized by dispersion in a flowing air or other physiologically acceptable gas stream in a conventional manner. One system suitable for such dispersion is described in copending application Ser. No. 07/910,048, which-has been published as WO 93/00951, the full disclosures of which are incorporated herein by reference. Referring to FIG. 1 herein, dry, free-flowing insulin powder is introduced into a high velocity air or gas stream, and the resulting dispersion introduced into a holding chamber 10. The holding chamber 10 includes a mouthpiece 12 at an end opposite to the entry point of the air powder dispersion. The volume of the chamber 10 is sufficiently large to capture a desired dose and may optionally have baffles and/or one-way valves for promoting containment. After a dose of the insulin powder has been captured in chamber 10, a patient P (FIG. 2) inhales on the mouthpiece 12 to draw the aerosolized dispersion into his lungs. As the patient P inhales, make-up air is introduced through a tangentially oriented air inlet port 14, whereby the air flows in a generally vortical pattern to sweep the aerosolized insulin from the chamber into the patient's lungs. The volume of the chamber and the aerosolized dose are such that a patient is able to completely inhale the entire aerosolized insulin dose followed by sufficient air to ensure that the insulin reaches the lower alveolar regions of the lung.

Such aerosolized insulin powders are particularly useful in place of subcutaneous injections of rapid acting insulin in the treatment of diabetes and related insulin-deficiencies. Surprisingly, it has been found that the aerosol administration of dry powder insulin results in significantly more rapid insulin absorption and glucose response than is achieved by subcutaneous injection. Thus, the methods and compositions of the present invention will be particularly valuable in treatment protocols where a patient monitors blood glucose levels frequently and administers insulin as needed to maintain a target serum concentration, but will also be useful whenever systemic insulin administration is required. The patient can achieve a desired dosage by inhaling an appropriate amount of insulin, as just described. The efficiency of systemic insulin delivery via the method as just described will typically be in the range from about 15% to 30%, with individual dosages (on a per inhalation basis), typically being in the range from about 0.5 mg to 10 mg. Usually, the total dosage of insulin desired during a single respiratory administration will be in the range from about 0.5 mg to 15 mg. Thus, the desired dosage may be effective by the patient taking from 1 breath to 4 breaths.

The following examples are offered by way of illustration, not by way of limitation.

EXPERIMENTAL

Materials and Methods

Materials

Crystalline human zinc insulin, 26.3 Units/mg, (Lilly Lot #784KK2) was obtained from Eli Lilly and Company, Indianapolis, Ind. and found to be >99% pure as measured by rpHPLC. USP mannitol was obtained from Roquette Corporation (Gurnee, Ill.). Raffinose was purchased from Pfanstiehl Laboratories (Waukegan, Ill.). Sodium citrate dihydrate, USP; ACS and citric acid monohydrate USP were obtained from J.T. Baker (Phillipsburg, N.J.).

Powder Production

Insulin powders were made by dissolving bulk crystalline insulin in sodium citrate buffer containing excipient (mannitol, or raffinose, or none) to give final solids concentration of 7.5 mg/ml and a pH of 6.7±0.3. The spray dryer was operated with an inlet temperature between 110° C. to 120° C. and a liquid feed rate of 5 ml/min, resulting in an outlet temperature between 70° C. and 80° C. The solutions were then filtered through a 0.22 μm filter and spray dried in a Buchi Spray Dryer to form a fine white amorphous powder. The resulting powders were stored in tightly capped containers in a dry environment (<10% RH).

Powder Analyses

The particle size distribution of the powders was measured by liquid centrifugal sedimentation in a Horiba CAPA-700 Particle Size Analyzer following dispersion of the powders in Sedisperse A-11 (Micromeritics, Norcross, Ga.).

The moisture content of the powders was measured by the Karl Fischer technique using a Mitsubishi CA-06 Moisture Meter.

The integrity of insulin before and after powder processing was measured against a reference standard of human insulin by redissolving weighed portions of powder in distilled water and comparing the redissolved solution with the original solution put into the spray dryer. Retention time and peak area by rpHPLC were used to determine whether the insulin molecule had been chemically modified or degraded in process. UV absorbance was used to determine insulin concentration (at 278 nm) and presence or absence of insoluble aggregates (at 400 nm). In addition, the pHs of the starting and reconstituted solutions were measured. The amorphous nature of the insulin powder was confirmed by polarizing light microscopy.

Rat Aerosol Exposures

Rat experiments were conducted in an aerosol exposure room. Female rats (280–300 μm) were fasted overnight. Animals (21–24/experiment) were placed in Plexiglas tubes and mounted into a 48 port, nose-only aerosol exposure chamber (In-Tox Products, Albuquerque, N. Mex.). Airflow to the breathing zone was maintained at 7.2–9.8 liters/minute and removed by vacuum so that there was a slight negative pressure (~1.5 cm $H_2O$) in the chamber as measured by a magnahelic gauge. Aerosol exposure times were between 5–20 minutes depending on how much powder was fed into the chamber. Powders were fed by hand into a small Venturi nozzle which dispersed the powder particles to form a fine aerosol cloud. The Venturi nozzle was operated at a pressure in excess of 15 psig, and the air flow was set at 7.2 l/min to 9.8 l/min. The Venturi nozzle was fitted into the bottom of a clear Plexiglas dispersion chamber (750 ml) which passed the aerosol directly into a nose-only exposure chamber.

Rat Aerosol Chamber Calibration

The concentration of the powder at the breathing zone was measured by taking multiple, timed filter samples at the breathing zone with In-Tox filter holders at a vacuum flow of 2 liters/min. The chamber was calibrated both with and without animals. Powder mass was determined gravimetrically. The particle size of the powders at the breathing zone was measured with cascade impactor (In Tox Products) placed at a breathing hole and operated at a flow of 2 liters/min. Powder mass on each stage was determined gravimetrically.

Each powder test utilized 21–24 rats and the aerosol exposures lasted 5–20 minutes. Three rats were killed at 0 time and then at ~7, 15, 30, 60, 90, 120, 180, and 240 minutes after the termination of the aerosol exposure. Animals were anesthetized, their abdomens opened, and a large blood sample was drawn from the ventral aorta. The animals were then killed by cervical dislocation.

Blood was allowed to clot at room temperature for 30 minutes and then centrifuged for 20 minutes at 3500 rpm in serum separator tubes. Serum was either analyzed immediately or frozen at −80° C. until analysis. As soon as possible (0–7 min) after the termination of the aerosol dosing, 3 rats were killed, their blood drawn and their lungs lavaged with six 5 ml rinses of phosphate buffered saline (PBS). The amount of insulin in the final pooled lavage sample was used as the aerosol dose for the rat in calculations of bioavailability.

Primate Exposure System

Young, wild-captured, male cynomolgus monkeys strain *Macaca fascicularis* (2–5 kg) (Charles River Primates, Inc.) were used for the primate aerosol studies (3–4 animals/group). The animals were either subcutaneously injected with Humulin (Eli Lilly, Indianapolis, Ind.) or exposed to a powder aerosol of insulin. Each animal was placed in a head-only exposure unit to provide a fresh supply of the test atmosphere at an adequate flow rate (7 L/min) to provide minimum oxygen requirements of the animal. The animals were restrained in a chair-like apparatus which placed them in an upright sitting position. The hoods were clear allowing the animals complete visualization of their environment. An indwelling catheter was placed in the leg so that blood samples could be taken at any time. The monkeys were fully awake during the whole procedure and appeared to be calm. Primate blood was treated the same as rat (see above).

The primate aerosol exposure system included a breath monitor that allowed quantification of the amount of air inhaled by each monkey. This value, coupled with measurements of the concentration of insulin in the inspired air allowed the calculation of exactly how much insulin was inhaled by each animal.

Human Trials

Insulin was administered to 24 normal human subjects subcutaneously as well as by inhalation of aerosolized dry insulin powders. Each subcutaneous injection consisted of 10.4 U of Humulin R, 100 U/ml (Eli Lilly, Indianapolis, Ind.). The dry insulin powders were amorphous and prepared by spray drying as described above with 20% by weight mannitol excipient. Doses (5 mg) of the insulin dry powder were dispersed in a high-velocity air stream to produce a fine aerosol that was captured in a chamber. Each subject inhaled the aerosol powder by taking a slow, deep breath of each aerosol bolus or "puff." Powder was administered in three puffs (for a dosage of 31.9 U). Serum insulin and glucose levels were determined over time, as described below.

Serum Assays

Serum insulin levels in rats, primates, and humans were determined using Coat-A-Count radio immunoassay kits for human insulin (Diagnostic Products Corporation, Los Angeles, Calif.). Standard curves were run with every batch of samples. The sensitivity of the assay was approximately 43 pg/ml. The within assay variability (%CV) is <5%. Glucose assays were performed by California Veterinary Diagnostics, Inc. in West Sacramento, Calif. using the Glucose/HK Reagent System Pack for the Boehringer Mannheim/Hitachi 747 Analyzer. The within assay variability (%CV) is <3%.

In the rate experiments, relative bioavailabilities of the aerosol were calculated by comparing the dose adjusted, immunoreactive insulin (IRI) area under the curve (AUC) of the concentration-time profile with that obtained from subcutaneous injection. In rats the total lavaged insulin mass was used as the aerosol dose. Some insulin is absorbed before the lungs can be lavaged so the dose estimated by this technique is probably a slight underestimate of the total deposited dose. No corrections for this presumed loss were made.

In the monkey experiments, relative bioavailabilities were calculated similar to the rats above except that instead of using lavaged lung insulin as the aerosol dose, the total amount of insulin inhaled was used. In the rats, only material deposited in the lungs, not insulin deposited in the nasal passages and throat, was included in the dose estimate. In the monkeys, all insulin that entered the animals was included in the dose estimate.

Results of Insulin Absorption in Rats

Figure 8A:
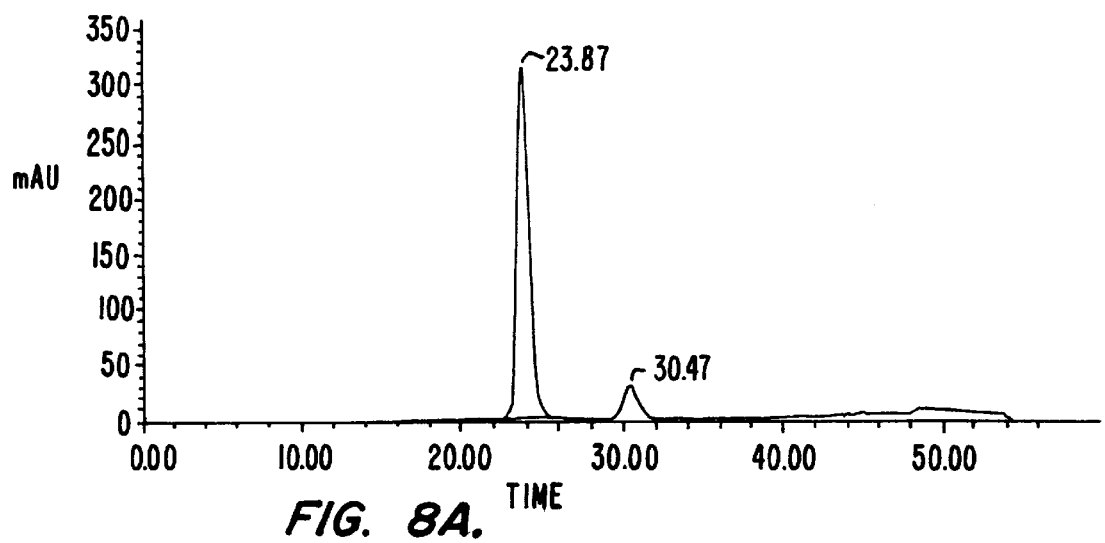
FIGS. 8A, 8B, and 8C show rpHPLC chromatograms of a human insulin.
Figure 8B:
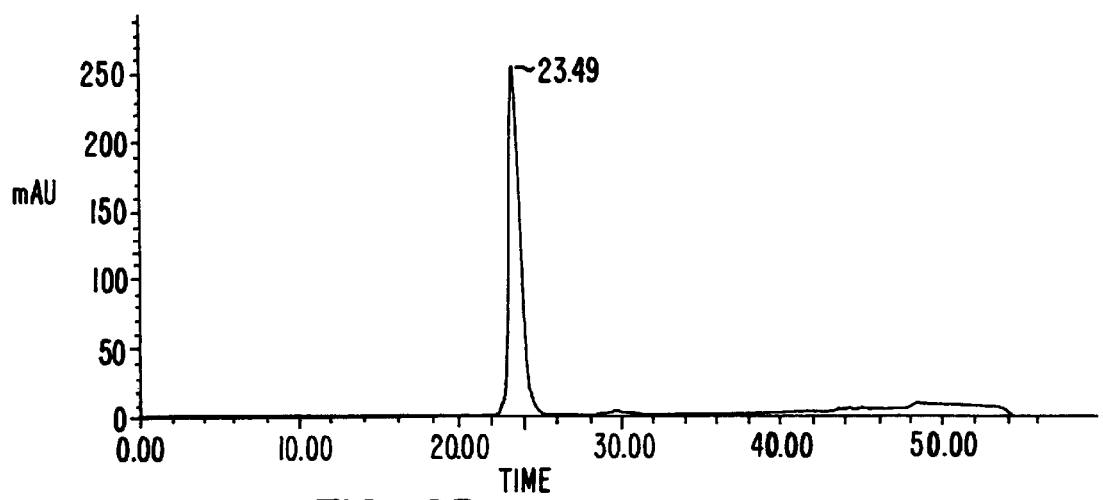
Figure 8C:
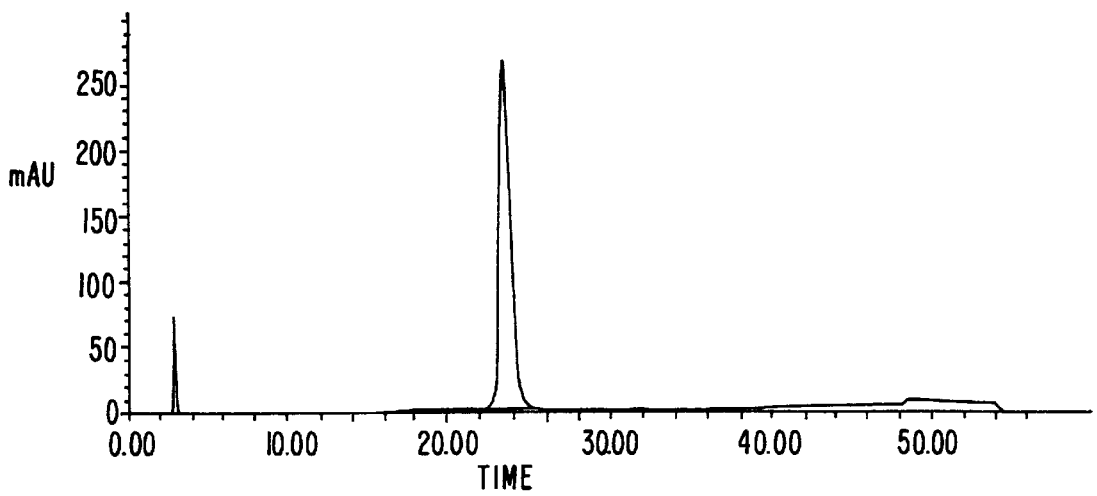
Figure 9:
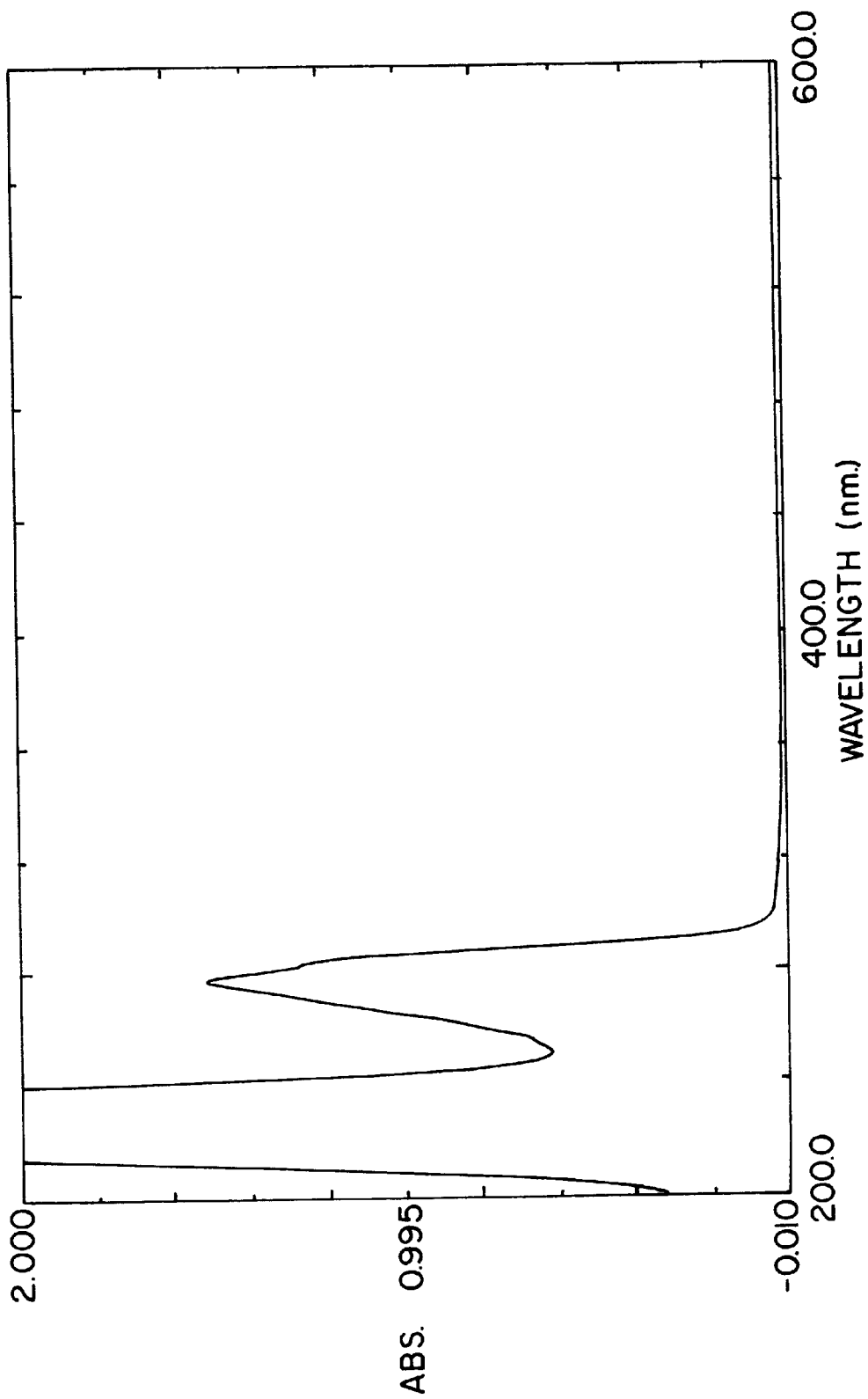
FIG. 9 shows an ultraviolet spectra of an insulin formulation before and after spray drying. No light scattering was observed in the visible spectrum, indicating that insulin did not aggregate during the spray drying process.

All of the insulin powders used in the animal studies had particle sizes (mass median diameters) ranging between 1–3 µm and moisture contents <3%. The insulin purity of the powders as measured by rpHPLC was >97%. Representative chromatographs of the 20% insulin formulation are shown in FIG. 8C. The powders yielded a clear solution upon reconstitution with pure water with an ultraviolet absorbance value <0.01 at 400 nm and a pH of 6.7±0.3. Representative ultraviolet (UV) spectra for the 20% insulin formulation are shown in FIG. 9.

The following three insulin powder formulations were tested in rats as aerosols in the In-Tox 48 port, exposure chamber.

1. 87.9% insulin; 11.5% sodium citrate; 0.6% citric acid.
2. 20% insulin; 66% mannitol: 12.4% sodium citrate: 0.6% citric acid.
3. 20% insulin; 66% raffinose; 12.4% sodium citrate: 0.6% citric acid.

Table 1 lists the key measurements in the three different rat exposure studies including characterizations of the aerosol at the breathing zone and chamber operating conditions. A fraction of the powder fed into the venturi nozzle reached the breathing zones of the rats (34%–67%) because of losses in the walls due to impaction and incomplete dispersion of the powder during powder feed. The particle size of the aerosol at the breathing zone, however, was ideal for pulmonary deposition (1.3–1.9 µm) and was somewhat smaller than the original formulation particle size (2.0–2.8 µm) due to selective loss of the larger particles in the animal exposure chamber.

Figure 3A:
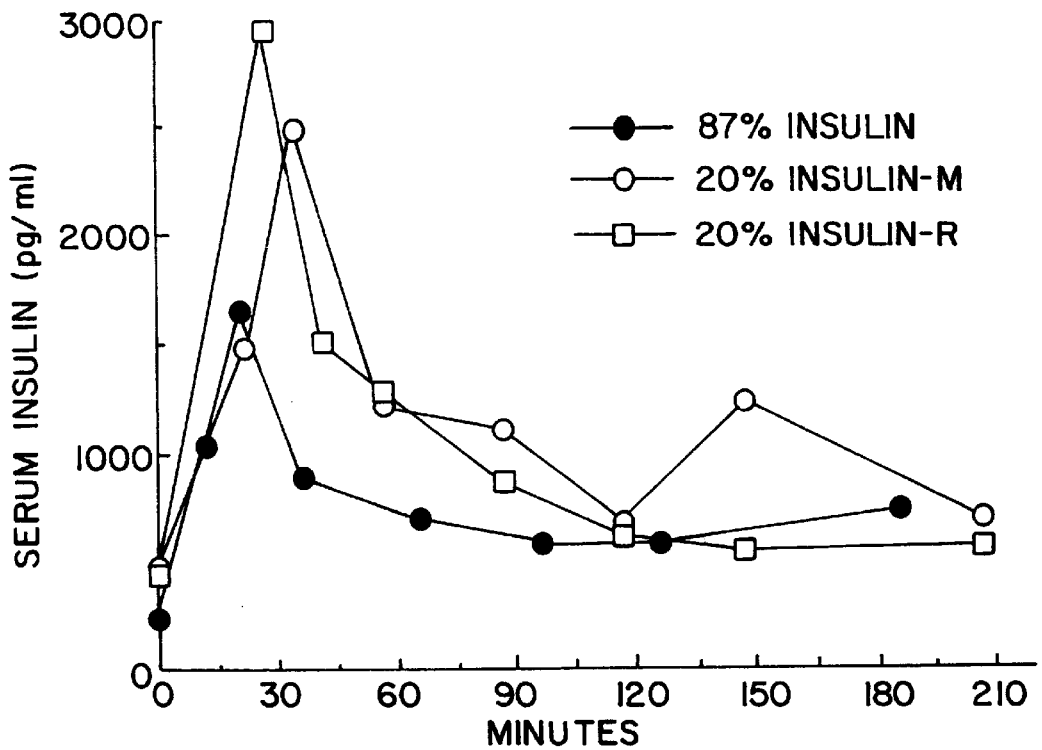
FIGS. 3A and 3B are graphs illustrating the absorption of recombinant human insulin in rats and resulting glucose response following aerosolization of three different dry powder formulations. Each point represents the mean value from three different rats. At zero time, the dry powder aerosol generator was turned on. Aerosolization was complete at 5 min, 14 min and 20 min for the 87% insulin/citrate, 20% insulin-mannitol/citrate and 20% insulin-raffinose/citrate powders, respectively. Animals were fasted overnight.
Figure 3B:
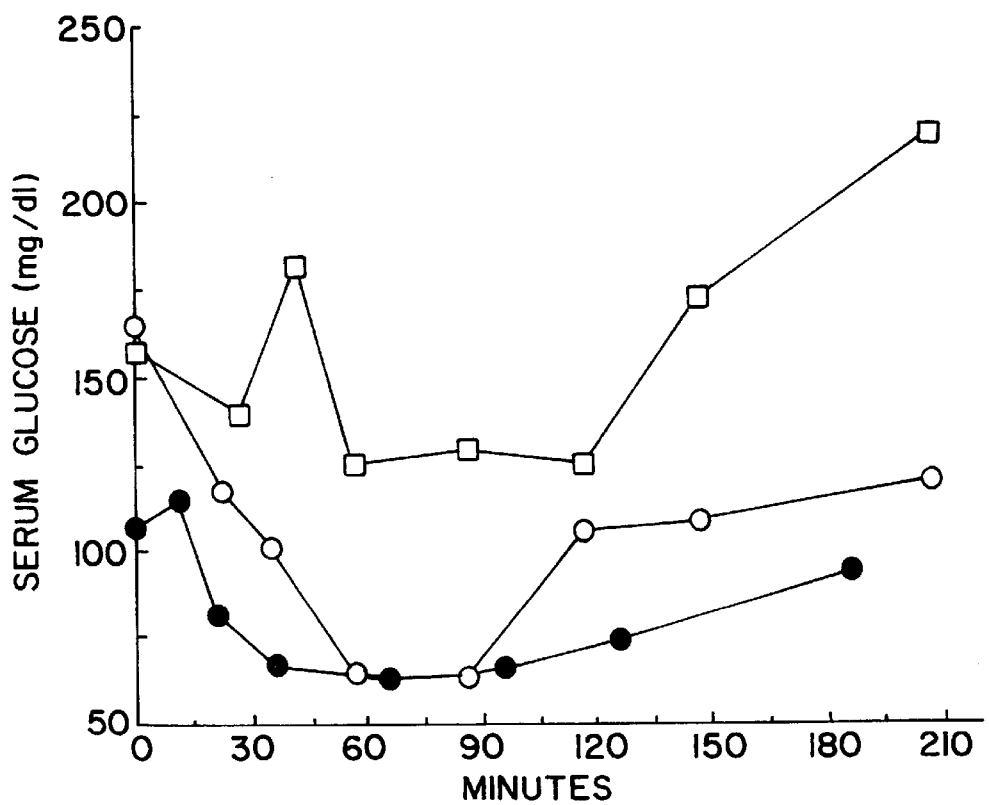

Table 2 shows the rat serum insulin and glucose results from the three aerosol and one SC study. FIG. 3A and 3B show the serum immunoreactive insulin (IRI) concentration-time profiles and the serum glucose concentration-time profiles for the three formulations administered by aerosol. Table 3 presents the insulin $t_{max}$, and the glucose $t_{min}$ from the different studies as well as the relative bioavailability of the aerosol compared to SC injection.

TABLE 1

Rat Aerosol Exposure Measurements

|  | 88% Insulin | 20% Insulin Mannitol | 20% Insulin Raffinose |
|---|---|---|---|
| Chamber Flow Rate | 7.2 L/min | 9.6 L/min | 9.8 L/min |
| Powder Mass Median Diameter (MMD) | 2.2 µm | 2.8 µm | 2.0 µm |
| Powder Fed into Chamber | 70 mgs | 255 mgs | 260 mgs |
| Powder Feed Time | 5 min | 14 min | 20 min |
| Powder at Breathing Zone | 40 mgs | 171 mgs | 88 mgs |
| Insulin at Breathing Zone | 35 mgs | 34 mgs | 18 mgs |
| % Total Powder at Breathing Zone | 57% | 67% | 34% |
| Mass Median Aerodynamic Diameter (MAD) | 1.1 µm | 1.3 µm | 0.42 µm |
| Particle Size at Breathing Zone | 1.4 µm | 1.9 µm | 1.3 µm |
| Insulin Recovered in Lavage | 30.7 ± 5.2 µg | 12.7 ± 6.9 µg | 31.6 ± 12.9 µg |
| Serum Insulin AUC (ng min/ml) | 104 | 201 | 150 |

TABLE 2

Serum Insulin and Glucose Results in Rats

| Formulation | Route | Time (min) | Serum Insulin (pg/ml ± 1 S.D.) n = 3 rats/timept | Serum Glucose (mg/dl ± 1 S.D.) n = 3 rats/timept |
|---|---|---|---|---|
| 88% Insulin | Aerosol | 0 | 230 ± 184 | 106 ± 12 |
| (Aerosol exposure | Aerosol | 12 | 1020 ± 312 | 114 ± 10 |
| completed at minute | Aerosol | 21 | 165 ± 768 | 81 ± 10 |
| 5) |  |  |  |  |
| Av. Dose = 31 µg/rat | Aerosol | 36 | 876 ± 764 | 66 ± 7 |
|  | Aerosol | 66 | 684 ± 416 | 62 ± 15 |
|  | Aerosol | 96 | 568 ± 128 | 65 ± 10 |
|  | Aerosol | 126 | 564 ± 260 | 73 ± 11 |
|  | Aerosol | 186 | 712 ± 140 | 93 ± 5 |
| 20% Insulin-Mannitol | Aerosol | 0 | 476 ± 56 | 165 ± 18 |
| (Aerosol exposure | Aerosol | 22 | 1476 ± 428 | 117 ± 15 |
| completed at minute | Aerosol | 35 | 2480 ± 892 | 101 ± 19 |
| 14) |  |  |  |  |
| Av. Dose = 13 µg/rat | Aerosol | 57 | 1204 ± 64 | 64 ± 13 |
|  | Aerosol | 87 | 1084 ± 396 | 63 ± 17 |
|  | Aerosol | 117 | 664 ± 180 | 105 ± 38 |
|  | Aerosol | 147 | 1228 ± 416 | 108 ± 22 |
|  | Aerosol | 207 | 676 ± 100 | 119 ± 33 |
| 20% Insulin-Raffinose | Aerosol | 0 | 426 ± 97 | 157 ± 37 |
| (Aerosol exposure | Aerosol | 27 | 2948 ± 2816 | 139 ± 46 |
| completed at minute | Aerosol | 42 | 1504 ± 592 | 181 ± 11 |
| 20) |  |  |  |  |
| Av. Dose = 32 µg/rat | Aerosol | 57 | 1272 ± 496 | 124 ± 45 |
|  | Aerosol | 87 | 852 ± 164 | 128 ± 17 |
|  | Aerosol | 117 | 604 ± 156 | 124 ± 9 |
|  | Aerosol | 147 | 532 ± 172 | 172 ± 12 |
|  | Aerosol | 207 | 556 ± 100 | 218 ± 34 |
| 20% Insulin-Mannitol | Subcutan | 0 | 360 ± 140 | 107 ± 5 |
| Dose = 30 µg | Subcutan | 15 | 14200 ± 3160 | 53 ± 2 |
| Insulin/rat |  |  |  |  |
|  | Subcutan | 30 | 10160 ± 720 | 24 ± 5 |
|  | Subcutan | 60 | 11000 ± 1080 | 28 ± 6 |
|  | Subcutan | 90 | 2440 ± 1160 | 25 ± 7 |
|  | Subcutan | 120 | 3520 ± 840 | 49 ± 3 |
|  | Subcutan | 180 | 1280 ± 800 | 40 ± 17 |
|  | Subcutan | 240 | 400 ± 260 | 77 ± 34 |

TABLE 3

A Comparison of Aerosol and Subcutaneous (SC) Insulin in Animals

| | Rat SC | Rat Aerosol 88% Insulin | Rat Aerosol 20% Insulin Mannitol | Rat Aerosol 20% Insulin Raffinose | Monkey SC | Monkey Aerosol 20% Insulin Mannitol |
|---|---|---|---|---|---|---|
| Insulin Max* | 15 min | 16 min | 21 min | 17 min | 15 min | 30 min |
| Glucose Min.* | 30 min | 31 min | 43 min | 37 min | 45 min | 45 min |
| Glucose Drop | 77% | 42% | 62% | 21% | 45% | 73% |
| Rel Bioavail. | 100% | 10%** | 44%** | 14%** | 100% | 12%*** |

*T's measured from end of aerosol exposure period.
Glucose min = time to >85% of maximal reduction observed in study
**Based on insulin recovered by lavage from lung at end of aerosol exposure
*Based on insulin inhaled, includes losses in nasal passages and throat All three formulations provided rapid absorbing insulin to the rats systemic circulation (FIGS. 3A and 3**B). The bioavailability and glucose response were higher for the 20% insulin/mannitol powder (Table 3), although without performing many replicate experiments, it is uncertain if the difference was significant.

Primate Results

Figure 4A:
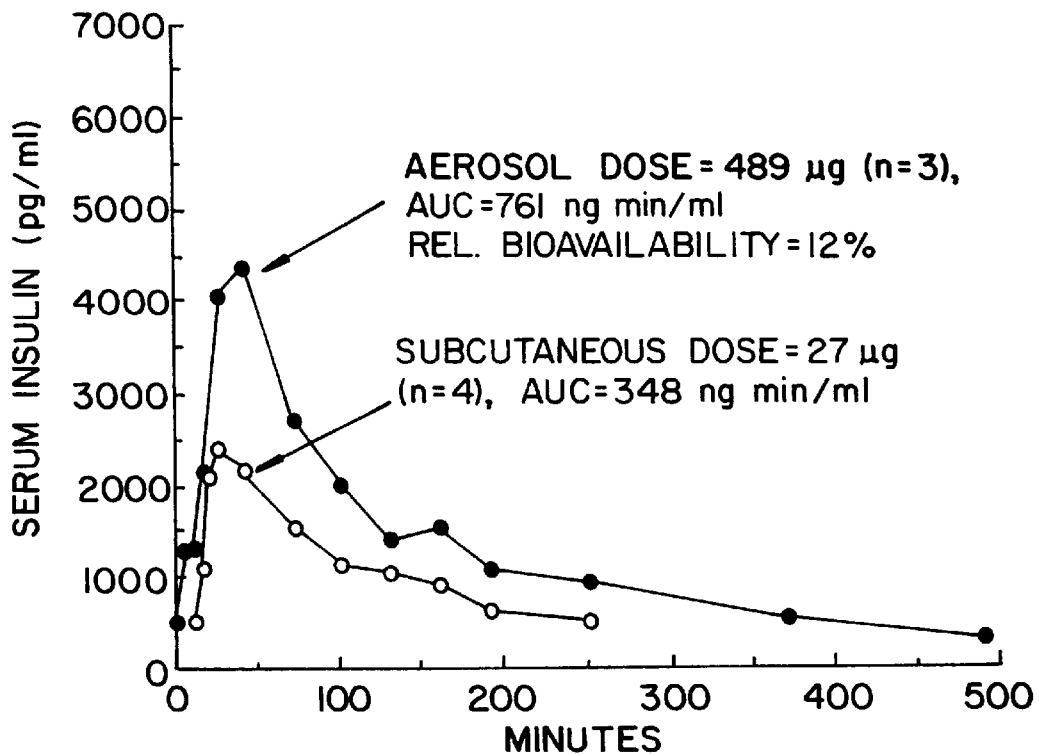
FIGS. 4A and 4B are graphs illustrating mean serum time-concentration insulin and glucose profiles, respectively comparing aerosol and subcutaneous administrations in cynomolgus monkeys. The mean value for three monkeys is reported for the aerosol group, and the mean value for four monkeys is reported for the subcutaneous group.
Figure 4B:
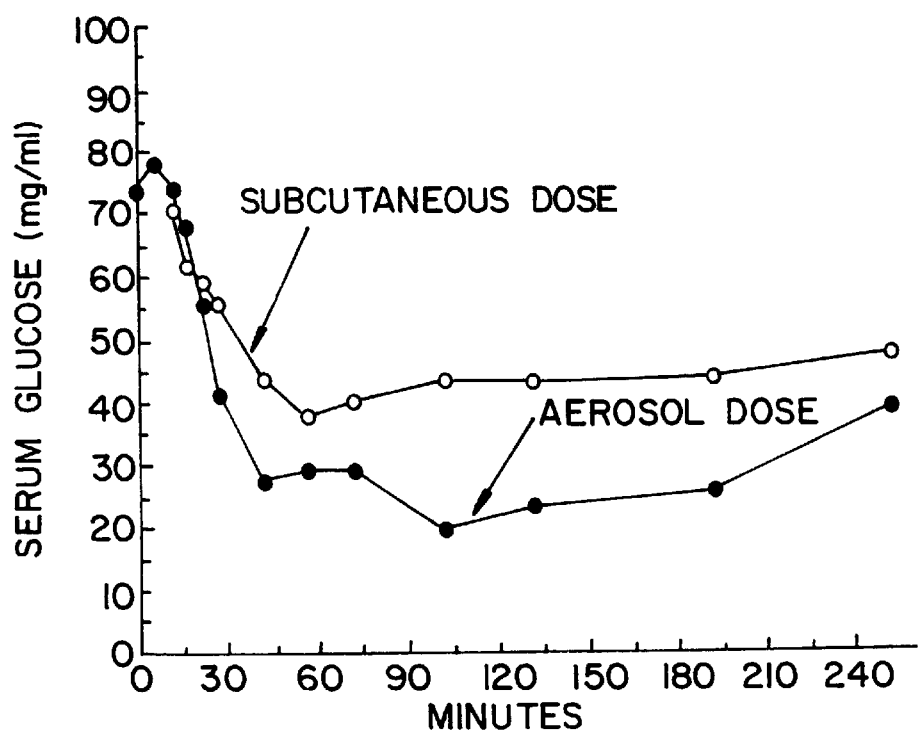

A dose identical to what was used in the human trial (0.2 U/kg, ~27 μg/monkey) was injected into four monkeys to provide the SC data with which to compare the aerosol results (FIGS. 4A and 4B). Table 4 shows the monkey aerosol exposure data. Table 5 shows the mean serum insulins and glucoses for the aerosol exposure and the subcutaneous study. The aerosol dose yielded a robust insulin and glucose response (high dose). FIG. 4 shows a comparison of the mean serum insulin profiles from the two aerosol and one SC study. From the AUCs of these profiles the relative bioavailability of the aerosol insulin was calculated to be 12%.

TABLE 4

Monkey Aerosol Exposure Data

| Animal ID | Grav. filter Mass (mg) | Avg Aerosol Conc. (μg/L) | Inhaled Volume (L) | Est. Inhaled Aerosol Mass (μg) | Est. Inhaled Insulin Mass (μg) | Body Wt. (Kg) | Est. Insulin Dose (μg/kg) | AUC (ng min/ ml) |
|---|---|---|---|---|---|---|---|---|
| #1, 23–46 | 1.07 | 178 | 8.96 | 1597 | 320 | 3.92 | 81.5 | 347 |
| #2, 23–48 | 1.01 | 168 | 19.98 | 3363 | 673 | 3.81 | 176.6 | 1196 |
| #3, 122–55 | 0.97 | 162 | 14.68 | 2373 | 475 | 4.1 | 115.7 | 739 |
| | | | | | 489 ± 178 | | | |

Human Results

The comparative results between respiratory delivery and subcutaneous injection are set forth in Table 5 below. Respiratory aerosol delivery resulted in more rapid absorption (peak at 20 minutes) than injection (peak at 60 minutes) with a more rapid glucose response (trough at 60 minutes) than with injection (trough at 90 minutes). Reproducibility was as good if not better with aerosol than with injection in both insulin and glucose response. Injection doses were carefully adjusted for weight, aerosol doses were not. Biological activity of aerosol insulin, based on glucose response, relative to injection was 28–36%. Bioavailability of aerosol insulin, based on area-under-the-insulin curve, relative to injection was 22.8% for the 3 puff group.

TABLE 5

Serum Insulin and Glucose Results in Humans

| INSULIN Subject #s | Dose/Injection or Blister | Dose in Subject* | Increase in Serum Insulin μU/ml | Time of Maximum | Relative Bioavailability Based on Insulin AUC |
|---|---|---|---|---|---|
| 1–24 (SC Injection) | 10.4 U | 10.4 U | 5.8–20.9 | 60 min | 100.0% |
| 7–24 (3 puffs) | 76.0 U | 31.9 U | 6.1–28.5 | 20 min | 22.8% |

| GLUCOSE Subject #s | Drop in Mean Serum Glucose mg/dl | mg/dl drop | Time of Minimum | % SC | Relative Bioactivity Based on Glucose Drop |
|---|---|---|---|---|---|
| 1–24 (SC Injection) | 93.6–64.9 | 28.7 | 90 min | 100% | 100% |
| 7–24 (3 puffs) | 91.8–67.6 | 24.2 | 60 min | 84.3% | 27.4% |

*Device Eff = 42%

Figure 5A:
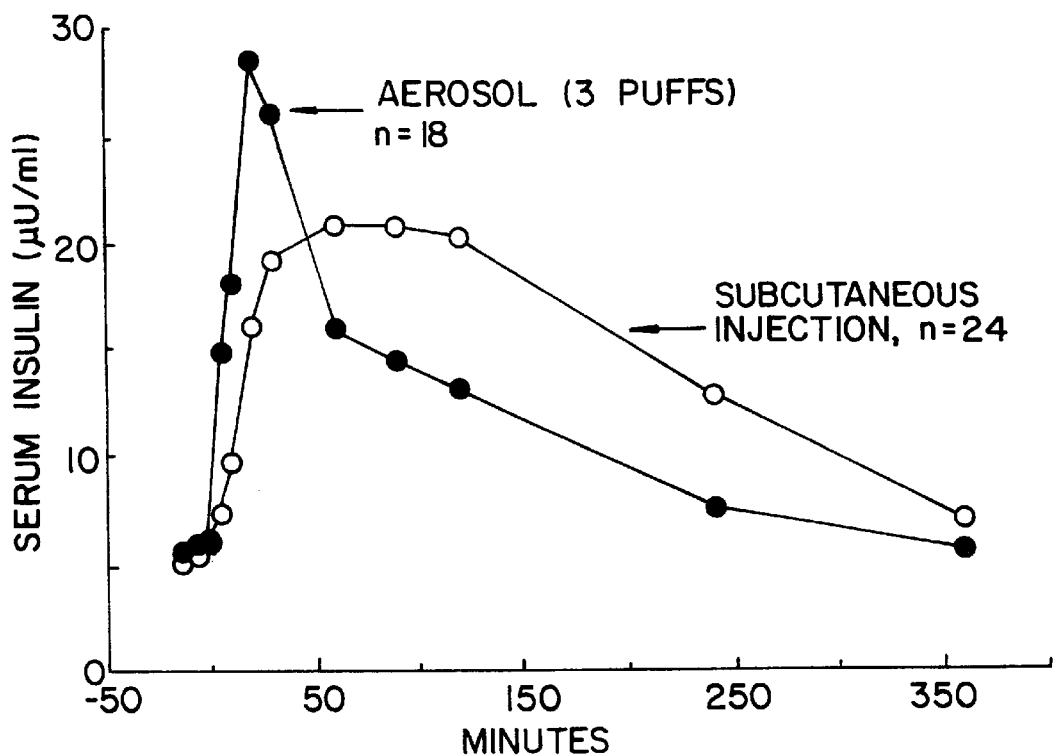
FIG. 5A is a graph illustrating the mean insulin concentration over time for subcutaneous injection (○) and for inhalation of three puffs (●) in humans.
Figure 5B:
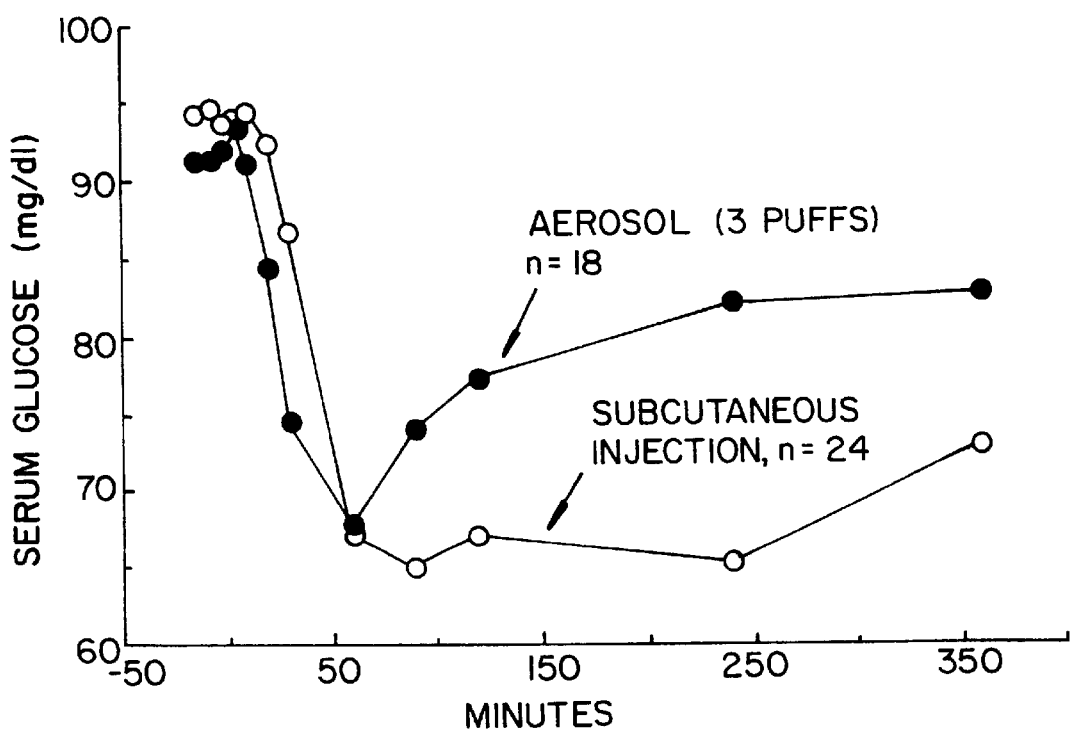
FIG. 5B shows the mean glucose concentration corresponding to the insulin concentrations of FIG. 5A.
Figure 6A:
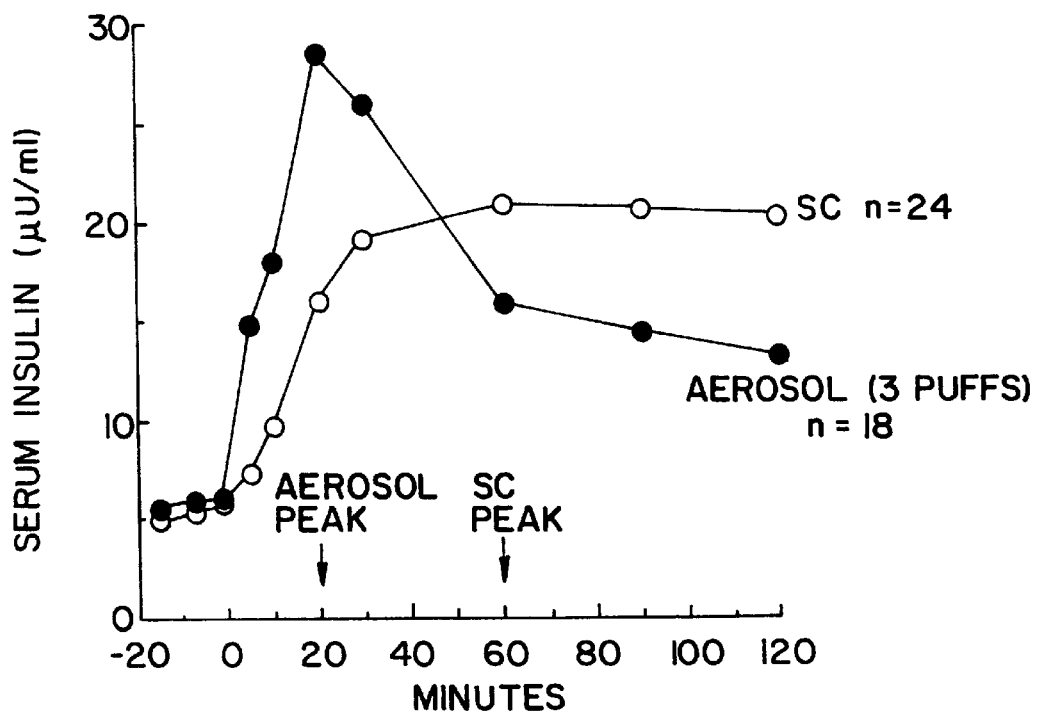
FIG. 6A is a graph illustrating serum insulin concentration over time as a result of subcutaneous injection (○) and three puffs of aerosol administration (●) in humans.
Figure 6B:
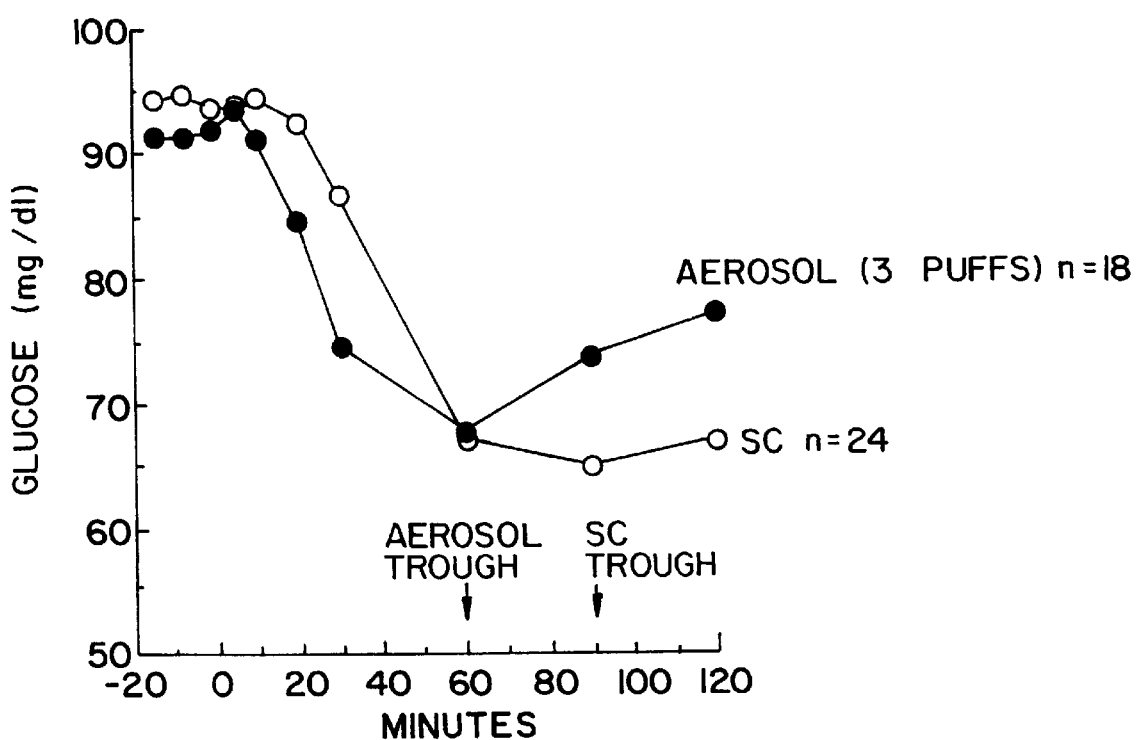
FIG. 6B is a graph illustrating the serum glucose levels corresponding to the insulin levels in FIG. 6A.
Figure 7A:
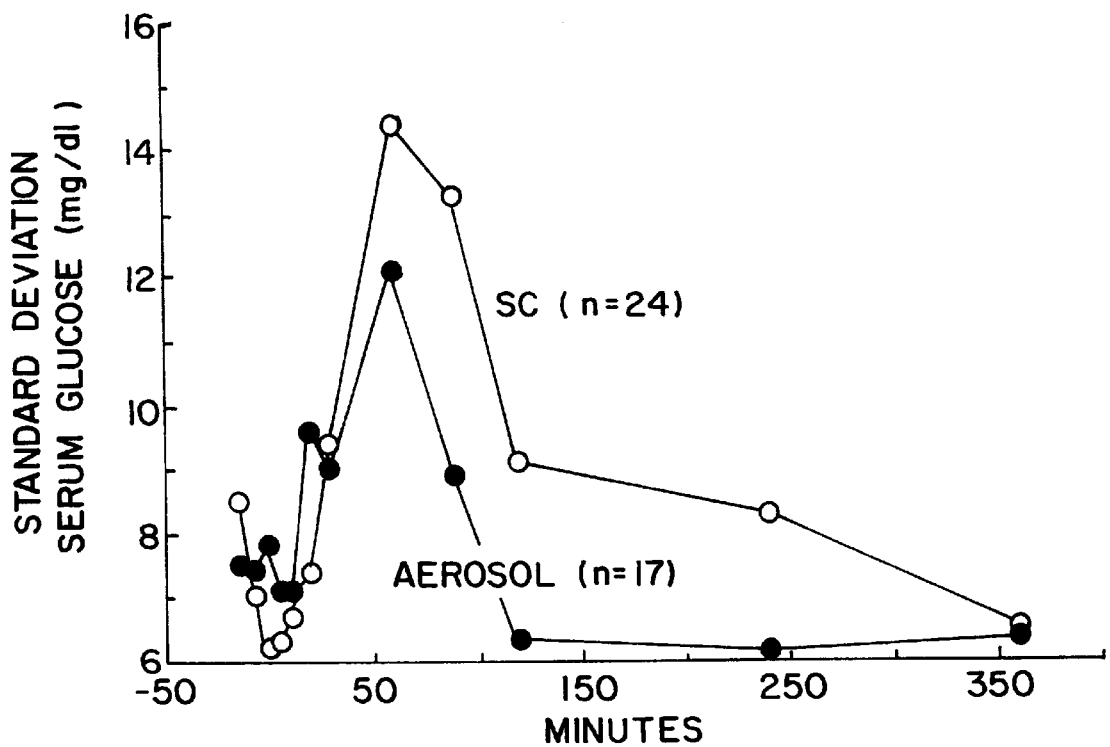
FIGS. 7A and 7B provide a comparison of the intersubject variability of serum insulin (7A) and glucose levels (7B) for subcutaneous administration (○) and aerosol administration (●).
Figure 7B:
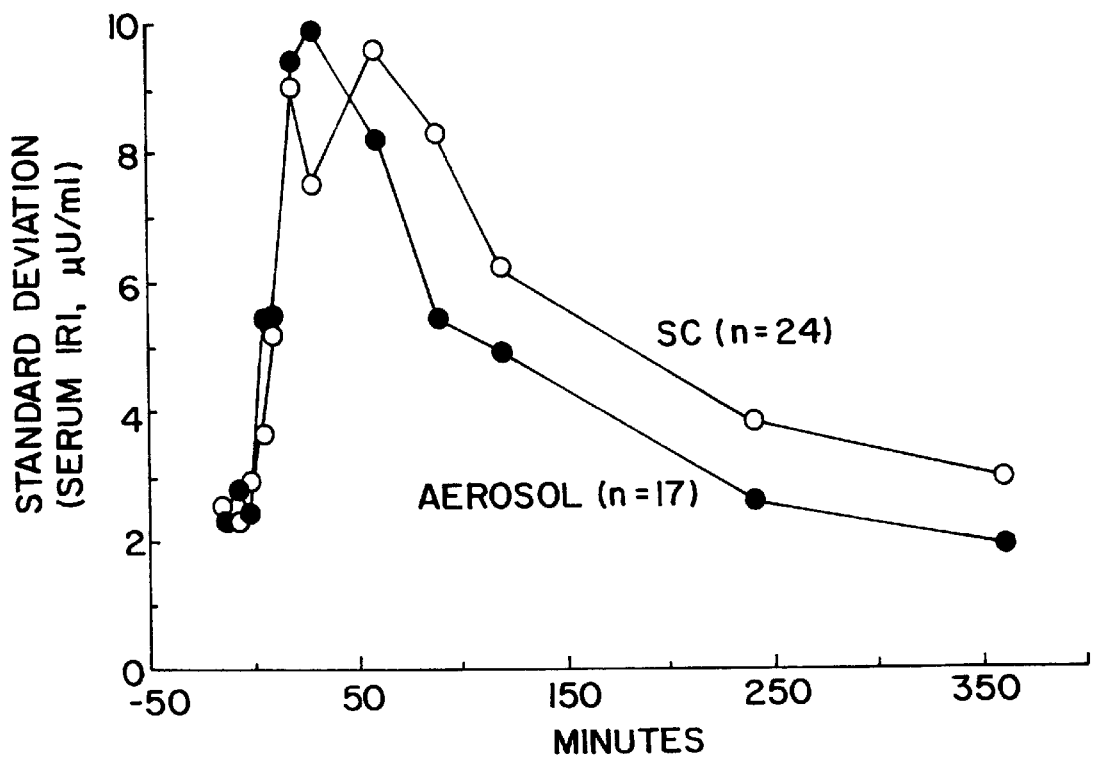

The results of the human trials are further presented in FIGS. 5A–5B. FIG. 5A shows mean serum insulin over time for subcutaneous injection (○), inhalation (3 puffs, ●). Mean serum glucose levels are similarly presented in FIG. 5B. Insulin peaks and glucose troughs are shown in FIGS. 6A and 6B, respectively, while intersubject variability in serum insulin and glucose are presented in FIGS. 7A and 7B, respectively.

In addition, the shallow inspirations (tidal breathing) of the monkeys during the aerosol exposures do not represent the optimal breathing maneuver for deep lung deposition. A higher bioavailability was observed in humans (Table 5), as expected, when the optimum breathing maneuver was used and the aerosol bolus was taken by oral inhalation rather than by nasal inhalation.

Although the foregoing invention has been described in some detail by way of illustration and example, for purposes of clarity of understanding, it will be obvious that certain changes and modifications may be practiced within the scope of the appended claims.

What is claimed is:

1. A method for delivering insulin into blood circulation of a patient, said method comprising:

providing from 1 to 4 individual dry powder insulin dosages having from a total weight of from 0.5 mg to 15 mg of insulin;

dispersing each of the dry powder insulin doses individually into a gas stream to form dry insulin aerosols; and inhaling each of the dry powder insulin aerosols into an alveolar region of the patient's lungs;

wherein the dry insulin powder dissolves in a fluid lining of the alveolar region of the lungs and is systemically absorbed into patient blood circulation.

2. A method as in claim 1, wherein the insulin is substantially free from penetration enhancers.

3. A method as in claim 1, wherein each dose contains from 0.5 mg to 10 mg of insulin.

4. A method as in claim 3, wherein the powder carrier comprises a carbohydrate, organic salt, amino acid, peptide, or protein.

5. A method as in claim 1, wherein the insulin dry powder comprises particles having an average size below 10 μm.

6. A method as in claim 1, wherein the dry powder comprises individual particles including both insulin and a carrier material.

7. A method as in claim 1, wherein the insulin is present in the individual particles at from 5% to 99% by weight.

* * * * *